United States Patent
Barrall et al.

(10) Patent No.: US 12,226,766 B2
(45) Date of Patent: Feb. 18, 2025

(54) REMOVING AND REINSERTING PROTEIN NANOPORES IN A MEMBRANE USING OSMOTIC IMBALANCE

(71) Applicant: Roche Sequencing Solutions, Inc., Pleasanton, CA (US)

(72) Inventors: Geoffrey Barrall, San Diego, CA (US); Takeshi Harada, San Jose, CA (US); Jason Komadina, Fremont, CA (US); Pirooz Parvarandeh, Los Altos Hills, CA (US); Charlotte Yang, San Jose, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 882 days.

(21) Appl. No.: 16/853,624

(22) Filed: Apr. 20, 2020

(65) Prior Publication Data
US 2020/0246791 A1  Aug. 6, 2020

Related U.S. Application Data

(63) Continuation of application No. PCT/EP2018/078925, filed on Oct. 22, 2018.
(Continued)

(51) Int. Cl.
*B01L 3/00* (2006.01)
*C12Q 1/6869* (2018.01)

(52) U.S. Cl.
CPC ............ *B01L 3/502* (2013.01); *C12Q 1/6869* (2013.01); *B01L 2200/12* (2013.01);
(Continued)

(58) Field of Classification Search
CPC ................ B01L 3/502; B01L 2200/12; B01L 2200/143; B01L 2300/044;
(Continued)

(56) References Cited

U.S. PATENT DOCUMENTS

| | | | |
|---|---|---|---|
| 2013/0048499 A1* | 2/2013 | Mayer | G01N 15/131 204/549 |
| 2015/0337366 A1* | 11/2015 | Davis | G01N 33/5432 435/6.19 |

(Continued)

FOREIGN PATENT DOCUMENTS

| | | |
|---|---|---|
| JP | 2011501806 A | 1/2011 |
| JP | 2015517799 A | 6/2015 |

(Continued)

OTHER PUBLICATIONS

Heginbathom, L. (1999). "Single *Streptomyces lividans* K+ channels Functional Asymmetries and Sidedness of Proton Activation." J Gen Physiol. 114. 551-559. (Year: 1999).*

(Continued)

*Primary Examiner* — Jill A Warden
*Assistant Examiner* — Jacqueline Brazin
(74) *Attorney, Agent, or Firm* — FisherBroyles LLP; Jason M. Pass; Gregory Thomas Fettig

(57) ABSTRACT

Techniques for replacing nanopores within a nanopore based sequencing chip are provided. A first electrolyte solution is added to the external reservoir of the sequencing chip, introducing an osmotic imbalance between the reservoir and the well chamber located on the opposite side of a lipid bilayer membrane. The osmotic imbalance causes the membrane to change shape, and a nanopore within the membrane to be ejected. A second electrolyte solution is then added to the external reservoir to provide replacement nanopores and to restore the membrane shape. The replacement nanopores can be inserted into the membrane, effectively replacing the initial pore without causing the destruction of the membrane.

9 Claims, 12 Drawing Sheets

Related U.S. Application Data

(60) Provisional application No. 62/575,814, filed on Oct. 23, 2017.

(52) U.S. Cl.
CPC ... *B01L 2200/143* (2013.01); *B01L 2300/044* (2013.01); *B01L 2300/0663* (2013.01); *B01L 2300/0896* (2013.01); *B01L 2400/06* (2013.01)

(58) Field of Classification Search
CPC ..... B01L 2300/0663; B01L 2300/0896; B01L 2400/06; C12Q 1/6869
USPC ...................................................... 435/286.5
See application file for complete search history.

(56) References Cited

U.S. PATENT DOCUMENTS

| | | | |
|---|---|---|---|
| 2017/0227520 A1* | 8/2017 | Mir | G01N 33/48721 |
| 2017/0369944 A1* | 12/2017 | Barrall | G01N 33/48721 |
| 2018/0073072 A1 | 3/2018 | Huber et al. | |
| 2022/0396758 A1 | 12/2022 | Nivala et al. | |
| 2023/0227903 A1* | 7/2023 | Bowen | C12Q 1/6869 435/6.11 |
| 2024/0076729 A9* | 3/2024 | Bowen | C12Q 1/6869 |

FOREIGN PATENT DOCUMENTS

| | | |
|---|---|---|
| JP | 2017131182 A | 8/2017 |
| JP | 2016524469 A | 9/2021 |
| WO | 2006/100484 A2 | 9/2006 |
| WO | 2006100484 A3 | 5/2008 |
| WO | 2009045472 A1 | 4/2009 |
| WO | 2013185137 A1 | 12/2013 |
| WO | 2015/055981 A2 | 4/2015 |
| WO | 2015055981 A3 | 6/2015 |
| WO | 2016/034591 A2 | 3/2016 |
| WO | 2016/099672 A1 | 6/2016 |
| WO | 2016034591 A3 | 6/2016 |
| WO | WO-2017087908 A1 * | 5/2017 |

OTHER PUBLICATIONS

Braha, O et al., Designed protein pores as components for biosensors, Chem Biol, (1997), pp. 497-505, vol. 4 Issue 7.

Heginbotham, L et al., Single *Streptomyces lividans* K Functional Asymmetries and Sidedness of Proton Activation, J Gen Physiol, (1999), pp. 551-559, vol. 114 Issue 4.

Holden, M A et al, Direct Introduction of Single Protein Channels and Pores into Lipid Bilayers, JACS, (2005), pp. 6502-6503, vol. 127 Issue 18.

International Search Report and Written Opinion mailed Dec. 12, 2018 in corresponding PCT/EP2018/078925 filed Oct. 22, 2018, pp. 1-14.

Miller, C. et al., Functional Asymmetries ans Sidedness of Proton Activation, Functional Asymmetries ans Sidedness of Proton Activation, Sep. 27, 1999, -, 114.

* cited by examiner

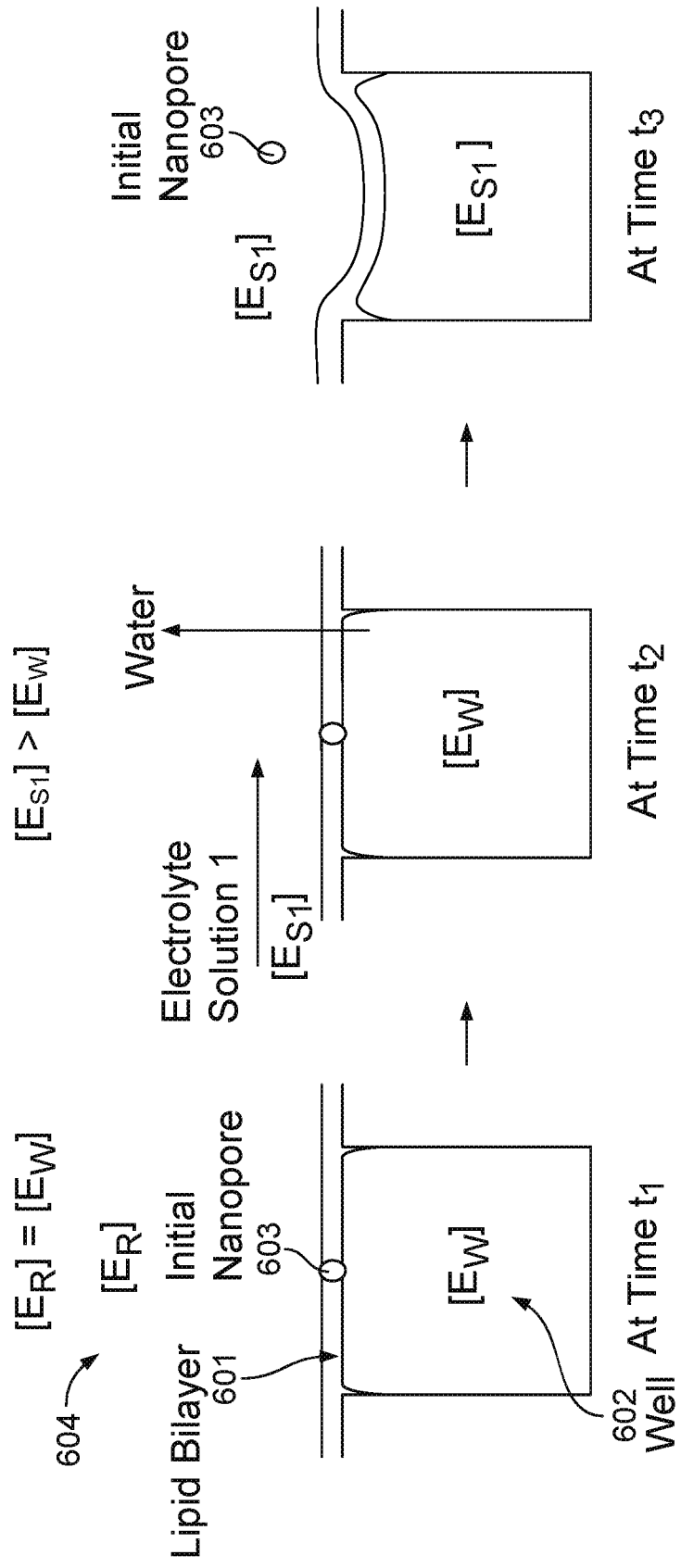

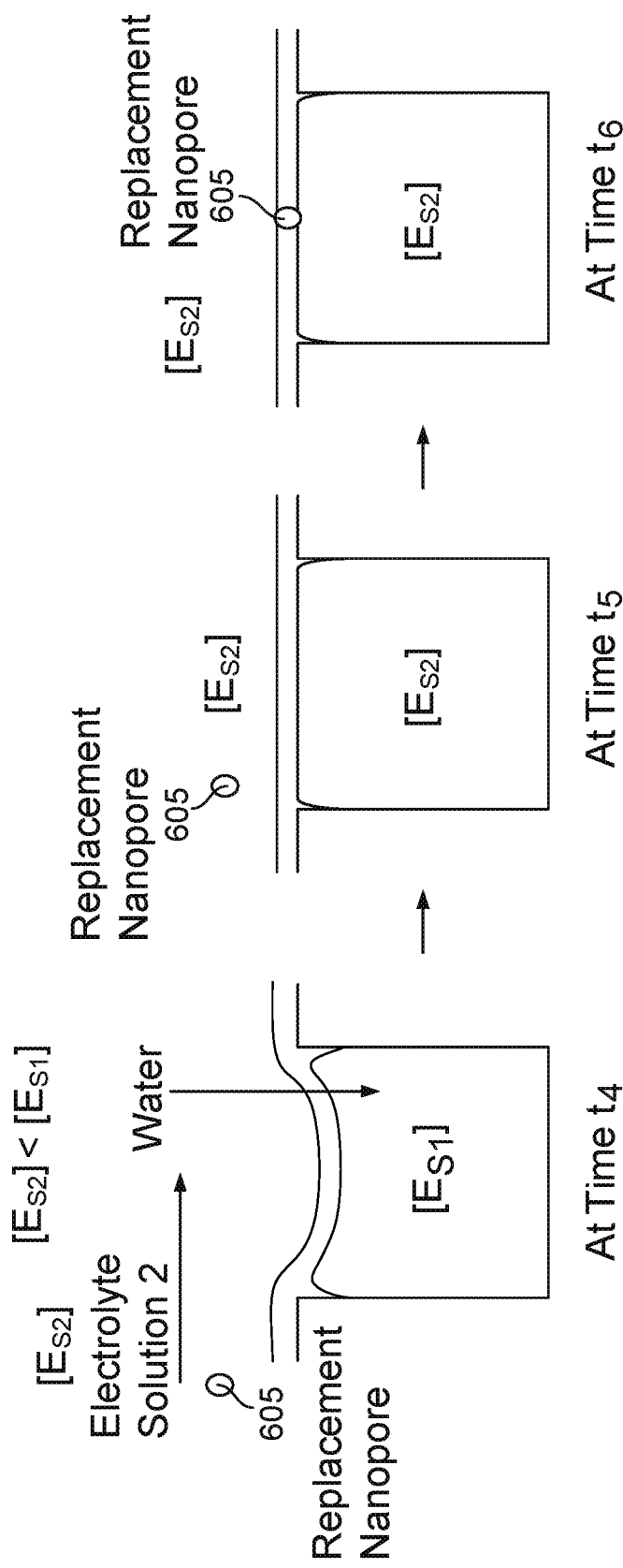

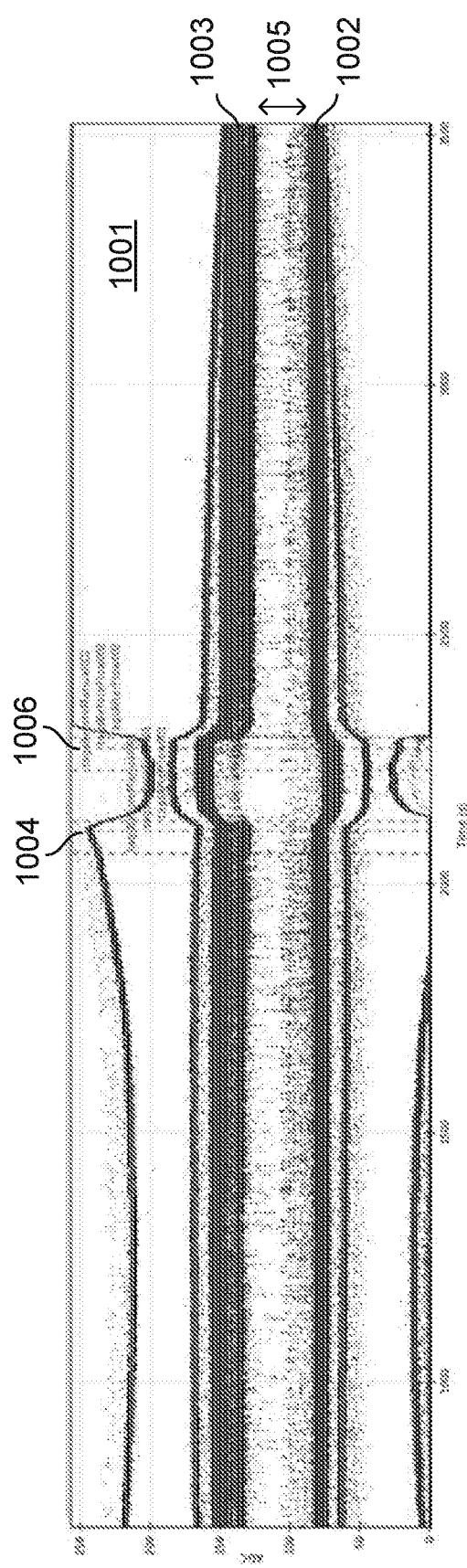
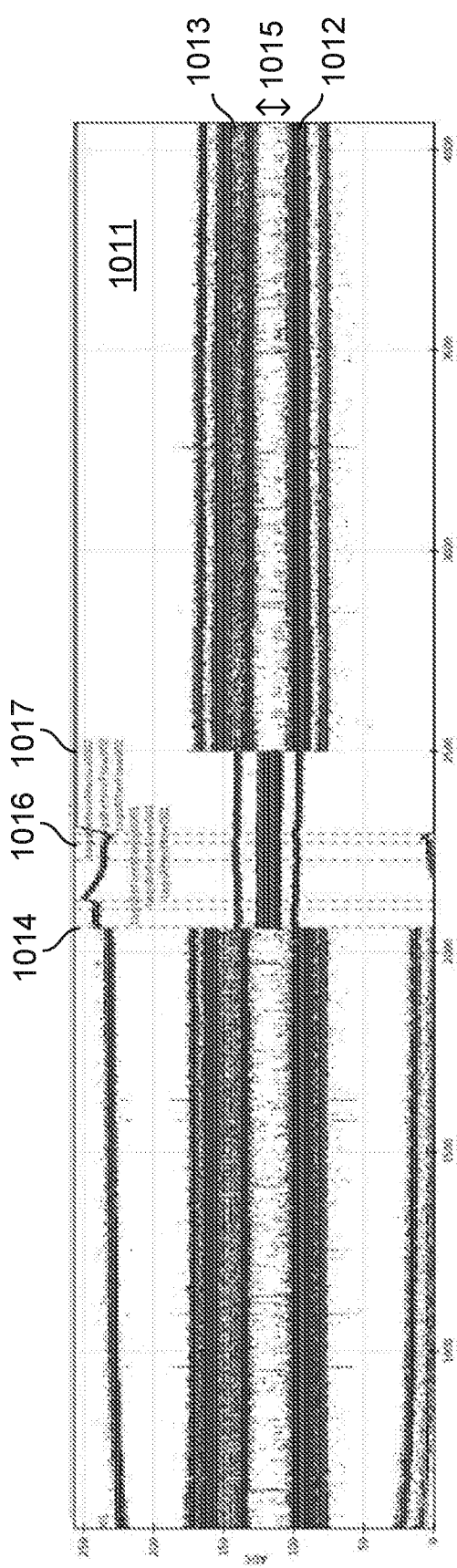
FIG. 10A
FIG. 10B

REMOVING AND REINSERTING PROTEIN NANOPORES IN A MEMBRANE USING OSMOTIC IMBALANCE

BACKGROUND

A nanopore based sequencing chip is an analytical tool that can be used for DNA sequencing. These devices can incorporate a large number of sensor cells configured as an array. For example, a sequencing chip can include an array of one million cells, with, for example, 1000 rows by 1000 columns of cells. Each cell of the array can include a membrane and a protein pore having a pore size on the order of one nanometer in internal diameter. Such nanopores have been shown to be effective in rapid nucleotide sequencing.

When a voltage potential is applied across a nanopore immersed in a conducting fluid, a small ion current attributed to the conduction of ions across the nanopore can exist. The size of the current is sensitive to the pore size and the type of molecule positioned within the nanopore. The molecule can be a particular tag attached to a particular nucleotide, thereby allowing detection of a nucleotide at a particular position of a nucleic acid. A voltage or other signal in a circuit including the nanopore can be measured (e.g., at an integrating capacitor) as a way of measuring the resistance of the molecule, thereby allowing detection of which molecule is in the nanopore.

Because this sequencing is dependent on the biochemical makeup of the sequencing chip nanopores, and their complexed template nucleic acids, the removal and replacement of nanopore complexes within a chip can enable the sequencing of additional nucleic acid molecules. One method for removing and reinserting pores into membranes is referred to as the patch-clamp method. However, the hydrostatic and electromotive forces of the patch-clamp method are not compatible with the pores and membranes found in chip based sensor arrays. Other standard techniques also cannot be used to controllably remove a protein nanopore inserted into a lipid bilayer membrane without necessitating the breaking and reforming of the bilayer.

Accordingly, improved pore removal and insertion techniques are desired to enable the replacement of pores within a membrane without causing membrane destruction.

BRIEF SUMMARY

Various embodiments provide techniques and systems related to the removal and replacement of nanopores and nanopore complexes in a nanopore based sequencing chip.

According to one embodiment, a first electrolyte solution is flowed to a first electrolyte reservoir that is divided from a second electrolyte reservoir by a membrane comprising an initial nanopore. The first reservoir initially has a first initial osmolarity, the second reservoir has a second initial osmolarity, and the first electrolyte solution has a first electrolyte solution osmolarity that is different than the first initial osmolarity. The flowing of the first electrolyte solution to the first reservoir changes the first electrolyte reservoir osmolarity from a first initial osmolarity to a new osmolarity that is different from the second initial osmolarity. The difference between the new and second initial osmolarities causes the membrane to bow in the direction of the second electrolyte reservoir, and the nanopore to eject from the membrane as a result of this bowing. In one example, the ratio of the first electrolyte solution osmolarity to the first initial osmolarity is within the range from 1.05 to 1.5. A second electrolyte solution is subsequently flowed to the first electrolyte reservoir, wherein the second electrolyte solution comprises a plurality of replacement nanopores, and wherein the second electrolyte solution has a second electrolyte solution osmolarity that is closer to the second initial osmolarity than the first electrolyte solution osmolarity. One of the plurality of replacement nanopores is then inserted into the membrane. In one embodiment, the insertion comprises applying an electroporation voltage across the membrane.

Other embodiments are directed to systems and computer readable media associated with methods described herein. For example, in some embodiments, a system for updating a sequencing cell includes a fluid chamber comprising a first electrolyte reservoir of the sequencing cell, a second electrolyte reservoir of the sequencing cell, and a membrane that divides the first electrolyte reservoir from the second electrolyte reservoir, where the membrane includes an initial nanopore, and where the first electrolyte reservoir has a first initial osmolarity and the second electrolyte reservoir has a second initial osmolarity. The system further includes a flow subsystem that controls a flow of a solution to the first electrolyte reservoir; a plurality of replacement nanopores; a voltage source configured to apply a voltage across the membrane; and control circuitry communicably coupled with the voltage source and the flow subsystem. The control circuitry causes the voltage source and the flow subsystem to perform operations including flowing a first electrolyte solution to the first electrolyte reservoir, wherein the first electrolyte solution has a first electrolyte solution osmolarity that is different than the first initial reservoir osmolarity, thereby causing the first electrolyte reservoir to have a new osmolarity that is different than the first initial osmolarity, so as to eject the initial nanopore from the membrane; adding a second electrolyte solution to the first electrolyte reservoir, wherein the second electrolyte solution includes the plurality of replacement nanopores, and wherein the second electrolyte solution has a second electrolyte solution osmolarity that is closer to the second initial osmolarity than the first electrolyte solution osmolarity; and applying a voltage across the membrane so as to insert one of the plurality of replacement nanopores into the membrane. In some embodiments, the system further includes a detector configured to record a measurement of an osmolarity, where the control circuitry is communicably connected to the detector. In some embodiments, the detector is configured to record a measurement of an osmolarity of an effluent exiting the first electrolyte reservoir. In some embodiments, the operations further include comparing the measurement to a preselected osmolarity for controlling a flow into the first electrolyte reservoir. In some embodiments, the operations further include generating a signal if the measurement exceeds or equals the preselected osmolarity; and stopping the flowing of the first electrolyte solution in response to the signal. In some embodiments, the operations further include generating a signal if the preselected osmolarity exceeds or equals the measurement; and stopping the flowing of the second electrolyte solution in response to the signal. In some embodiments, the system further includes one or more valves or pumps configured to adjust the flowing of the first electrolyte solution and the adding of the second electrolyte solution, where the control circuitry is communicably connected to each of the one or more valves or pumps. In some embodiments, the initial nanopore complex includes the initial nanopore, an initial template, and an initial polymerase; and where each of a plurality of replacement nanopore complexes includes one of the plurality of replacement nanopores, a replacement template, and a replacement polymerase. In some embodiments, the voltage source is an alternating current voltage source.

A better understanding of the nature and advantages of embodiments of the present invention can be gained with reference to the following detailed description and the accompanying drawings.

BRIEF DESCRIPTION OF THE DRAWINGS

FIG. 6A illustrates that at time $t_1$ of a method in accordance with an embodiment, an initial nanopore is inserted into a lipid bilayer spanning across a well in a cell of a nanopore based sequencing chip.

FIG. 6B illustrates that at time $t_2$, a first electrolyte solution having a lower osmolarity than that of the well solution is flowed into the reservoir external to the well, causing water to flow from the well into the external reservoir.

FIG. 6C illustrates that at time $t_3$, the shape of the lipid bilayer has changed to a degree sufficient to eject the initial nanopore.

FIG. 6D illustrates that at time $t_4$, a second electrolyte solution having replacement nanopores and an osmolarity identical or similar to that of the initial well solution is flowed into the reservoir external to the well, causing water to flow from the external reservoir into the cell.

FIG. 6E illustrates that at time $t_5$, the shape of the lipid bilayer has been substantially restored to its original configuration.

FIG. 6F illustrates that at time $t_6$, a replacement pore has been inserted into the lipid bilayer.

FIG. 10A is a graph plotting the ADC count over time for a sequencing cell without the ejection and replacement of a nanopore.

FIG. 10B is a graph plotting the ADC count over time for a sequencing cell with the ejection and replacement of a nanopore in accordance with an embodiment.

TERMS

Figure 1:
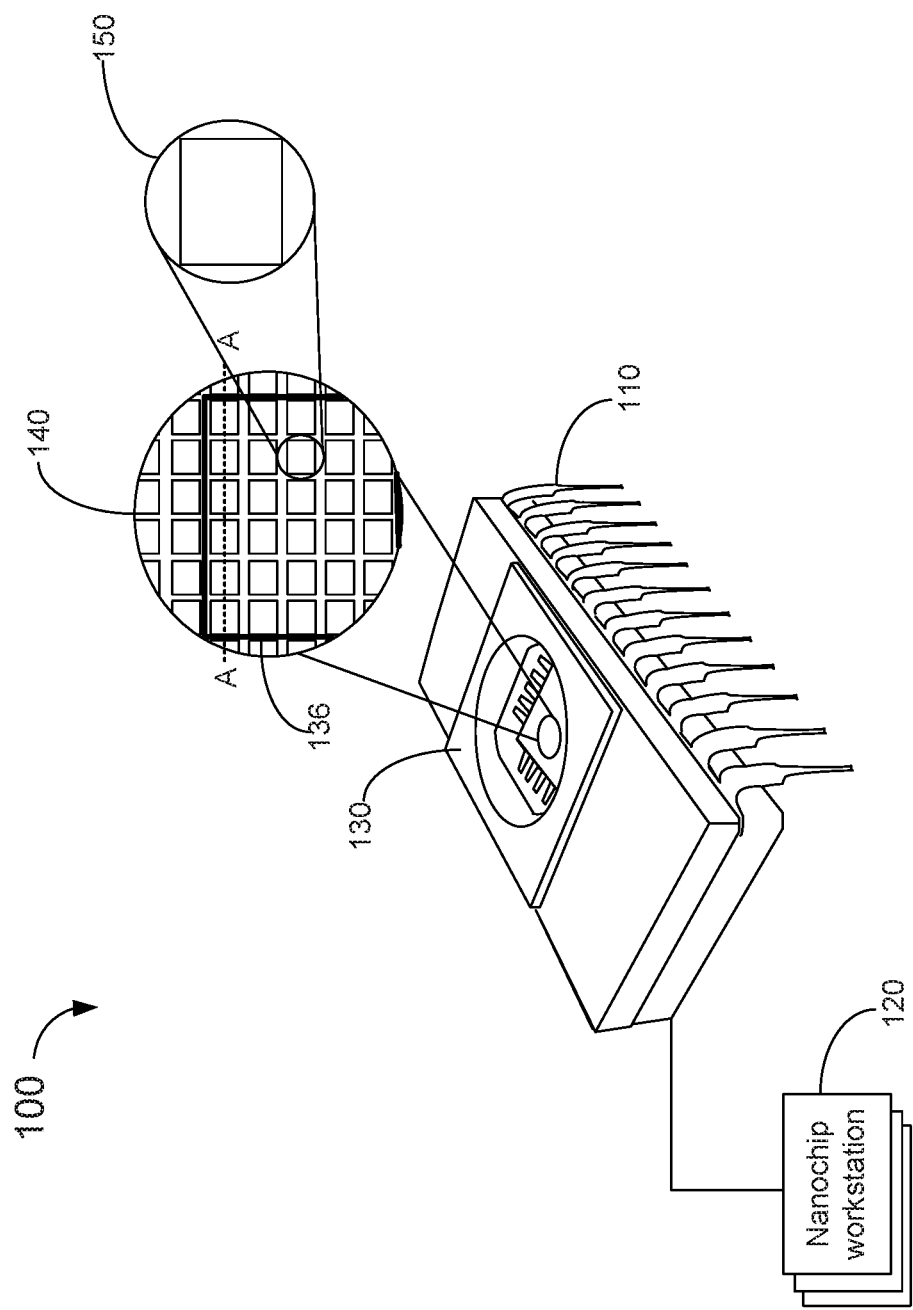
FIG. 1 is a top view of an embodiment of a nanopore sensor chip having an array of nanopore cells.

Unless defined otherwise, technical and scientific terms used herein have the same meaning as commonly understood by a person of ordinary skill in the art. Methods, devices, and materials similar or equivalent to those described herein can be used in the practice of disclosed techniques. The following terms are provided to facilitate understanding of certain terms used frequently and are not meant to limit the scope of the present disclosure. Abbreviations used herein have their conventional meaning within the chemical and biological arts.

A "nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. In some implementations, a nanopore may be a protein.

A "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidites, methyl phosphonates, chiral-methyl phosphonates, 2-O-methyl ribonucleotides, and peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid can be used interchangeably with gene, cDNA, mRNA, oligonucleotide, and polynucleotide.

The term "nucleotide," in addition to referring to the naturally occurring ribonucleotide or deoxyribonucleotide monomers, can be understood to refer to related structural variants thereof, including derivatives and analogs, that are functionally equivalent with respect to the particular context in which the nucleotide is being used (e.g., hybridization to a complementary base), unless the context clearly indicates otherwise.

The term "tag" refers to a detectable moiety that can be atoms or molecules, or a collection of atoms or molecules. A tag can provide an optical, electrochemical, magnetic, or electrostatic (e.g., inductive, capacitive) signature, which signature can be detected with the aid of a nanopore. Typically, when a nucleotide is attached to the tag it is called a "Tagged Nucleotide." The tag can be attached to the nucleotide via the phosphate moiety.

The term "template" refers to a single stranded nucleic acid molecule that is copied into a complementary strand of DNA nucleotides for DNA synthesis. In some cases, a template can refer to the sequence of DNA that is copied during the synthesis of mRNA.

The term "primer" refers to a short nucleic acid sequence that provides a starting point for DNA synthesis. Enzymes that catalyze the DNA synthesis, such as DNA polymerases, can add new nucleotides to a primer for DNA replication.

A "polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus, Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found—DNA polymerases I (family A), II (family B), and III (family C). In eukaryotic cells, three different family B polymerases—DNA polymerases α, β, and ε—are implicated in nuclear replication, and a family A polymerase—polymerase γ—is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

The term "bright period" generally refers to the time period when a tag of a tagged nucleotide is forced into a nanopore by an electric field applied through an AC signal. The term "dark period" generally refers to the time period when a tag of a tagged nucleotide is pushed out of the nanopore by the electric field applied through the AC signal. An AC cycle can include the bright period and the dark period. In different embodiments, the polarity of the voltage signal applied to a nanopore cell to put the nanopore cell into the bright period (or the dark period) can be different.

The term "signal value" refers to a value of the sequencing signal output from a sequencing cell. According to certain embodiments, the sequencing signal is an electrical signal that is measured and/or output from a point in a circuit of one or more sequencing cells e.g., the signal value is (or represents) a voltage or a current. The signal value can represent the results of a direct measurement of voltage and/or current and/or may represent an indirect measurement, e.g., the signal value can be a measured duration of time for which it takes a voltage or current to reach a specified value. A signal value can represent any measurable quantity that correlates with the resistivity of a nanopore and from which the resistivity and/or conductance of the nanopore (threaded and/or unthreaded) can be derived. As another example, the signal value can correspond to a light intensity, e.g., from a fluorophore attached to a nucleotide being added to a nucleic acid with a polymerase.

The term "osmolarity", also known as osmotic concentration, refers to a measure of solute concentration. Osmolarity measures the number of osmoles of solute particles per unit volume of solution. An osmole is a measure of the number of moles of solute that contribute to the osmotic pressure of a solution. Osmolarity allows the measurement of the osmotic pressure of a solution and the determination of how the solvent will diffuse across a semipermeable membrane (osmosis) separating two solutions of different osmotic concentration.

The term "osmolyte" refers to any soluble compound that when dissolved into a solution increases the osmolarity of that solution.

DETAILED DESCRIPTION

According to certain embodiments, techniques and systems disclosed herein relate to the removal and insertion of pores in membranes, such as lipid bilayer membranes. In applications such as DNA sequencing with a nanopore based sequencing chip, the ability to remove and replace a polymerase-pore complex without needing to reform membrane bilayers can enable increased analyte throughput. However, standard pore removal methods, such as those involving primarily hydrostatic or electromotive forces, typically cause the disruption or destruction of membranes. The reformation of these membranes then involves several additional steps, increasing the complexity and decreasing the efficiency of the process.

To address these issues, the methods provided herein can be used to nondestructively alter the shape of a membrane (e.g., a lipid bilayer) to the point at which a pore inserted within the membrane is no longer stable, and spontaneously ejects. This deformation of the membrane is achieved by replacing a solution on one side of the membrane with a new solution having a different osmolarity than that of the original solution. After the pore has been ejected, the original osmotic conditions of the solution can be restored, returning the membrane to its original shape without causing its breakage. A new pore can then be inserted into the membrane to replace the pore that has been removed. Because of the volume and concentration scales of the method, the likelihood of an ejected pore reinserting into the same membrane from which it was removed can be vanishingly small. The pore swapping techniques disclosed herein can be used to increase the throughput of single molecule sensor arrays in general, and of nanopore base sequencing chips in particular.

Example nanopore systems, circuitry, and sequencing operations are initially described, followed by example techniques to replace nanopores in DNA sequencing cells. Embodiments of the invention can be implemented in numerous ways, including as a process, a system, and a computer program product embodied on a computer readable storage medium and/or a processor, such as a processor configured to execute instructions stored on and/or provided by a memory coupled to the processor.

I. Nanopore Based Sequencing Chip

FIG. 1 is a top view of an embodiment of a nanopore sensor chip 100 having an array 140 of nanopore cells 150. Each nanopore cell 150 includes a control circuit integrated on a silicon substrate of nanopore sensor chip 100. In some embodiments, side walls 136 are included in array 140 to separate groups of nanopore cells 150 so that each group can receive a different sample for characterization. Each nanopore cell can be used to sequence a nucleic acid. In some embodiments, nanopore sensor chip 100 includes a cover plate 130. In some embodiments, nanopore sensor chip 100 also includes a plurality of pins 110 for interfacing with other circuits, such as a computer processor.

In some embodiments, nanopore sensor chip 100 includes multiple chips in a same package, such as, for example, a Multi-Chip Module (MCM) or System-in-Package (SiP). The chips can include, for example, a memory, a processor, a field-programmable gate array (FPGA), an application-specific integrated circuit (ASIC), data converters, a high-speed I/O interface, etc.

In some embodiments, nanopore sensor chip 100 is coupled to (e.g., docked to) a nanochip workstation 120, which can include various components for carrying out (e.g., automatically carrying out) various embodiments of the processes disclosed herein. These process can include, for example, analyte delivery mechanisms, such as pipettes for delivering lipid suspension or other membrane structure suspension, analyte solution, and/or other liquids, suspension or solids. The nanochip workstation components can further include robotic arms, one or more computer processors, and/or memory. A plurality of polynucleotides can be detected on array 140 of nanopore cells 150. In some embodiments, each nanopore cell 150 is individually addressable.

II. Nanopore Sequencing Cell

Nanopore cells 150 in nanopore sensor chip 100 can be implemented in many different ways. For example, in some embodiments, tags of different sizes and/or chemical structures are attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags both move through the nanopore, and an ion current passing through the nanopore can indicate the nucleotide that is in the nanopore because of the particular size and/or structure of the tag attached to the nucleotide. In some implementations, only the tags are moved into the nanopore. There can also be many different ways to detect the different tags in the nanopores.

A. Nanopore Sequencing Cell Structure

Figure 2:
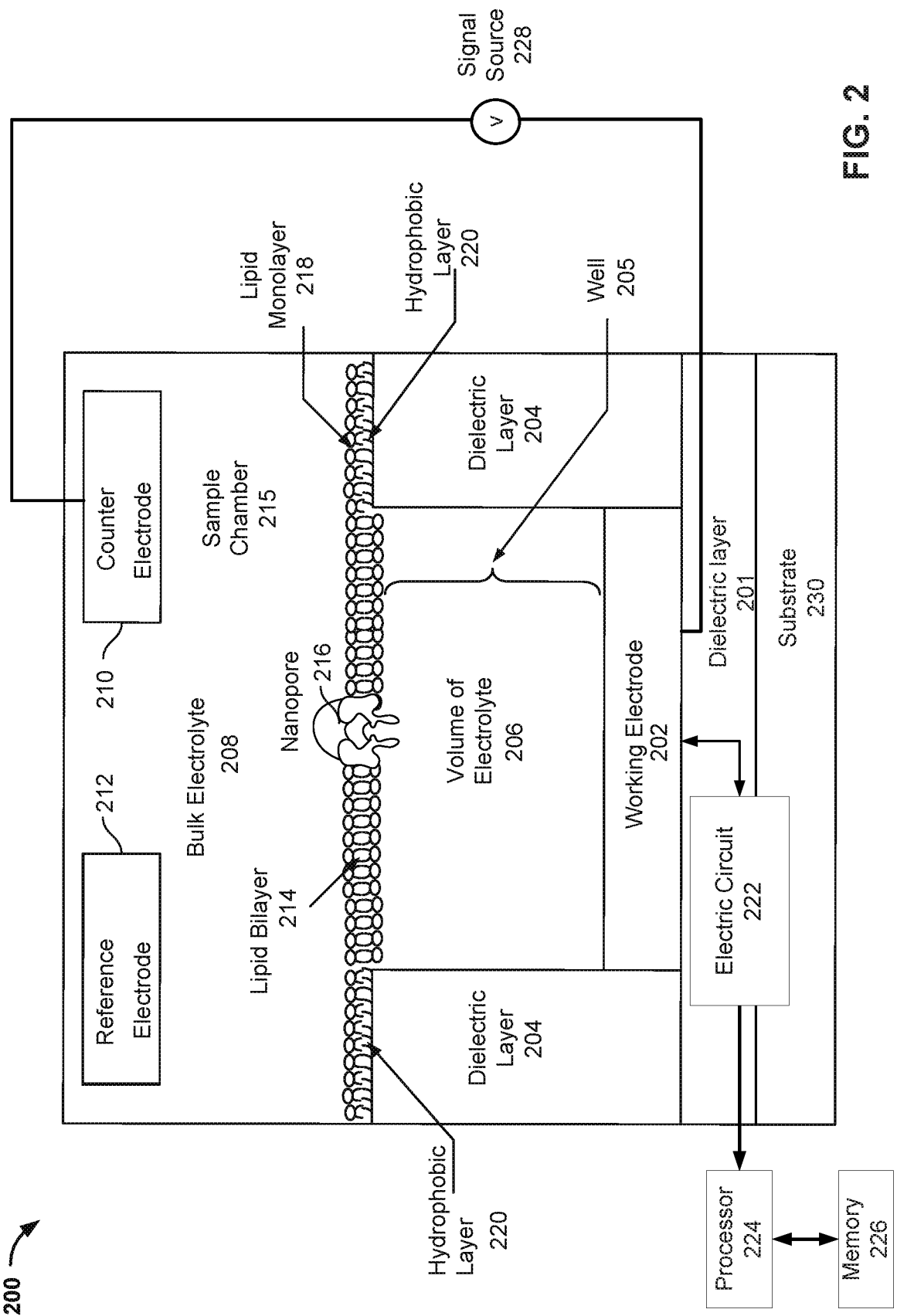
FIG. 2 illustrates an embodiment of a nanopore cell in a nanopore sensor chip that can be used to characterize a polynucleotide or a polypeptide.

FIG. 2 illustrates an embodiment of an example nanopore cell 200 in a nanopore sensor chip, such as nanopore cell 150 in nanopore sensor chip 100 of FIG. 1, that can be used to characterize a polynucleotide or a polypeptide. Nanopore cell 200 can include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 can contain a volume of electrolyte 206, and sample chamber 215 can hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 can include a working electrode 202 at the bottom of well 205 and a counter electrode 210 disposed in sample chamber 215. A signal source 228 can apply a voltage signal between working electrode 202 and counter electrode 210. A single nanopore (e.g., a PNTMC) can be inserted into lipid bilayer 214 by an electroporation process caused by the voltage signal, thereby forming a nanopore 216 in lipid bilayer 214. The individual membranes (e.g., lipid bilayers 214 or other membrane structures) in the array can be neither chemically nor electrically connected to each other. Thus, each nanopore cell in the array can be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 can be formed on a substrate 230, such as a silicon substrate. Dielectric layer 201 can be formed on substrate 230. Dielectric material used to form dielectric layer 201 can include, for example, glass, oxides, nitrides, and the like. An electric circuit 222 for controlling electrical stimulation and for processing the signal detected from nanopore cell 200 can be formed on substrate 230 and/or within dielectric layer 201. For example, a plurality of patterned metal layers (e.g., metal 1 to metal 6) can be formed in dielectric layer 201, and a plurality of active devices (e.g., transistors) can be fabricated on substrate 230. In some embodiments, signal source 228 is included as a part of electric circuit 222. Electric circuit 222 can include, for example, amplifiers, integrators, analog-to-digital converters, noise filters, feedback control logic, and/or various other components. Electric circuit 222 can be further coupled to a processor 224 that is coupled to a memory 226, where processor 224 can analyze the sequencing data to determine sequences of the polymer molecules that have been sequenced in the array.

Working electrode 202 can be formed on dielectric layer 201, and can form at least a part of the bottom of well 205. In some embodiments, working electrode 202 is a metal electrode. For non-faradaic conduction, working electrode 202 can be made of metals or other materials that are resistant to corrosion and oxidation, such as, for example, platinum, gold, titanium nitride, and graphite. For example, working electrode 202 can be a platinum electrode with electroplated platinum. In another example, working electrode 202 can be a titanium nitride (TiN) working electrode. Working electrode 202 can be porous, thereby increasing its surface area and a resulting capacitance associated with working electrode 202. Because the working electrode of a nanopore cell can be independent from the working electrode of another nanopore cell, the working electrode can be referred to as cell electrode in this disclosure.

Dielectric layer 204 can be formed above dielectric layer 201. Dielectric layer 204 forms the walls surrounding well 205. Dielectric material used to form dielectric layer 204 can include, for example, glass, oxide, silicon mononitride (SiN), polyimide, or other suitable hydrophobic insulating material. The top surface of dielectric layer 204 can be silanized. The silanization can form a hydrophobic layer 220 above the top surface of dielectric layer 204. In some embodiments, hydrophobic layer 220 has a thickness of about 1.5 nanometer (nm).

Well 205 formed by the dielectric layer walls 204 includes volume of electrolyte 206 above working electrode 202. Volume of electrolyte 206 can be buffered and can include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). In some embodiments, volume of electrolyte 206 has a thickness of about three microns (μm).

As also shown in FIG. 2, a membrane can be formed on top of dielectric layer 204 and spanning across well 205. In some embodiments, the membrane includes a lipid monolayer 218 formed on top of hydrophobic layer 220. As the membrane reaches the opening of well 205, lipid monolayer 208 can transition to lipid bilayer 214 that spans across the opening of well 205. The lipid bilayer can comprise or consist of lipids, such as a phospholipid, for example, selected from diphytanoyl-phosphatidylcholine (DPhPC), 1,2-diphytanoyl-sn-glycero-3-phosphocholine, 1,2-di-O-phytanyl-sn-glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol, 1,2-dipalmitoyl-sn-glycero-3-phosphoethanolamine-N-[methoxy(polyethylene glycol)-350], 1,2-dipalmitoyl-sn-glycero-3-phosphoethanolamine-N-[methoxy(polyethylene glycol)-550], 1,2-dipalmitoyl-sn-glycero-3-phosphoethanolamine-N-[methoxy(polyethylene glycol)-750], 1,2-dipalmitoyl-sn-glycero-3-phosphoethanolamine-N-[methoxy(polyethylene glycol)-1000], 1,2-dipalmitoyl-sn-glycero-3-phosphoethanolamine-N-[methoxy(polyethylene glycol)-2000], 1,2-dioleoyl-sn-glycero-3-phosphoethanolamine-N-lactosyl, GM1 Ganglioside, Lysophosphatidylcholine (LPC), or any combination thereof. Other phospholipid derivatives may also be used, such as phosphatidic acid derivatives (e.g., DMPA, DDPA, DSPA), phosphatidylcholine derivatives (e.g., DDPC, DLPC, DMPC, DPPC, DSPC, DOPC, POPC, DEPC), phosphatidylglycerol derivatives (e.g., DMPG, DPPG, DSPG, POPG), phosphatidylethanolamine derivatives (e.g., DMPE, DPPE, DSPE DOPE), phosphatidylserine derivatives (e.g., DOPS), PEG phospholipid derivatives (e.g, mPEG-phospholipid, polyglycerin-phospholipid, functionalized-phospholipid, terminal activated-phospholipid), diphytanoyl phospholipids (e.g., DPhPC, DOPhPC, DPhPE, and DOPhPE), for example. In some embodiments, the bilayer can be formed using non-lipid based materials, such as amphiphilic block copolymers (e.g, poly(butadiene)-block-poly(ethylene oxide), PEG diblock copolymers, PEG triblock copolymers, PPG triblock copolymers, and poloxamers) and other amphiphilic copolymers, which may be nonionic or ionic. In some embodiments, the bilayer can be formed from a combination of lipid based materials and non-lipid based materials. In some embodiments, the bilayer materials can be delivered in a solvent phase including one or more organic solvents such as alkanes (e.g., decane, tridecane, hexadecane, etc.), and/or one or more silicone oils (e.g., AR-20).

As shown, lipid bilayer 214 is embedded with a single nanopore 216, e.g., formed by a single PNTMC. As described above, nanopore 216 can be formed by inserting a single PNTMC into lipid bilayer 214 by electroporation. Nanopore 216 can be large enough for passing at least a portion of the analyte of interest and/or small ions (e.g., Na$^+$, K$^+$, Ca$^{2+}$, Cl$^-$) between the two sides of lipid bilayer 214.

Sample chamber 215 is over lipid bilayer 214, and can hold a solution of the analyte of interest for characterization. The solution can be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 can further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride (CaCl$_2$), strontium chloride (SrCl$_2$), manganese chloride (MnCl$_2$), and magnesium chloride (MgCl$_2$).

Counter electrode (CE) 210 can be an electrochemical potential sensor. In some embodiments, counter electrode 210 is shared between a plurality of nanopore cells, and can therefore be referred to as a common electrode. In some cases, the common potential and the common electrode can be common to all nanopore cells, or at least all nanopore cells within a particular grouping. The common electrode can be configured to apply a common potential to the bulk electrolyte 208 in contact with the nanopore 216. Counter electrode 210 and working electrode 202 can be coupled to signal source 228 for providing electrical stimulus (e.g., voltage bias) across lipid bilayer 214, and can be used for sensing electrical characteristics of lipid bilayer 214 (e.g., resistance, capacitance, and ionic current flow). In some embodiments, nanopore cell 200 can also include a reference electrode 212.

In some embodiments, various checks are made during creation of the nanopore cell as part of calibration. Once a nanopore cell is created, further calibration steps can be performed, e.g., to identify nanopore cells that are performing as desired (e.g., one nanopore in the cell). Such calibration checks can include physical checks, voltage calibration, open channel calibration, and identification of cells with a single nanopore.

B. Detection Signals of Nanopore Sequencing Cell

Nanopore cells in nanopore sensor chip, such as nanopore cells 150 in nanopore sensor chip 100, can enable parallel sequencing using a single molecule nanopore based sequencing by synthesis (Nano-SBS) technique.

Figure 3:
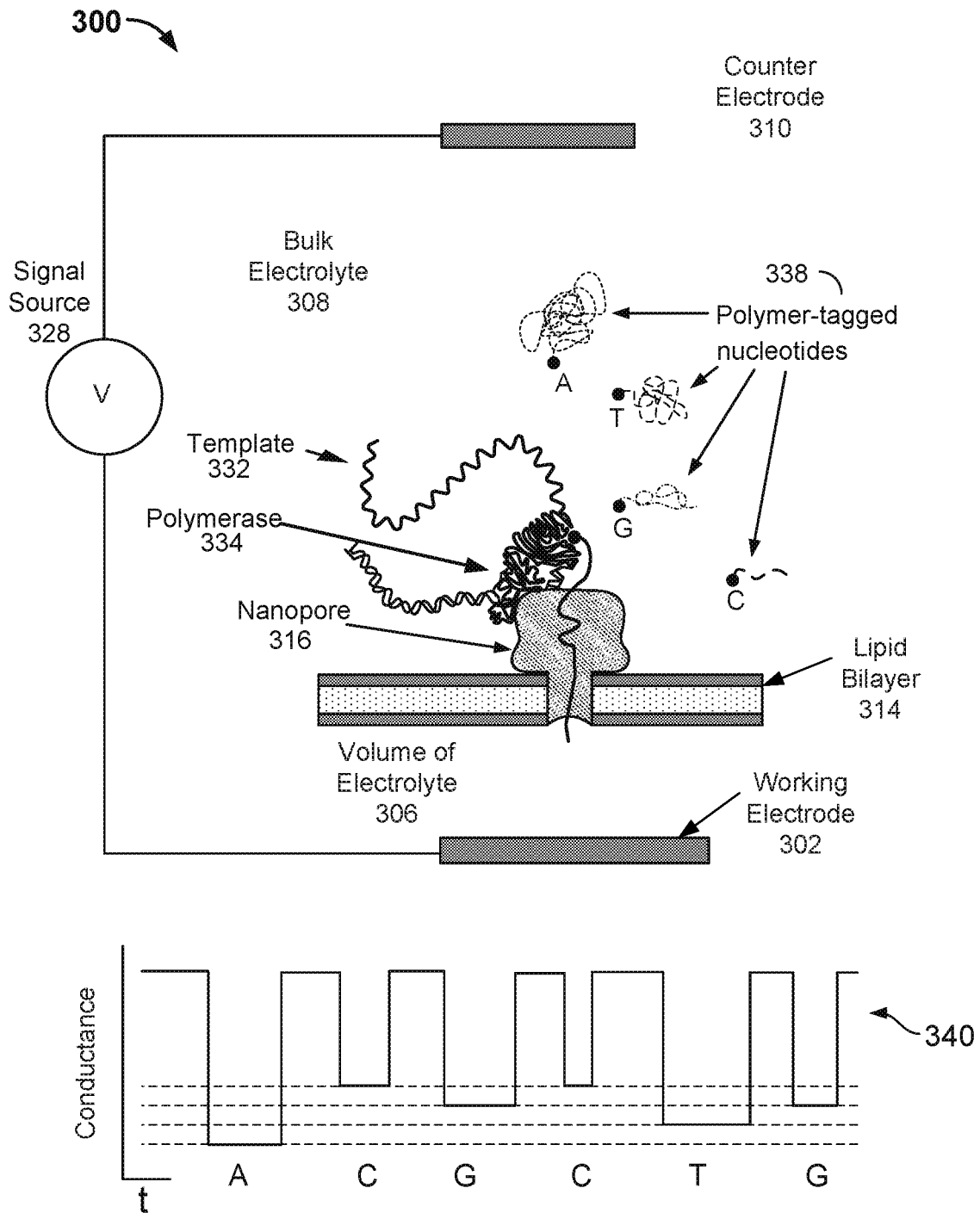
FIG. 3 illustrates an embodiment of a nanopore cell performing nucleotide sequencing using a nanopore based sequencing-by-synthesis (Nano-SBS) technique.

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer can be introduced into bulk electrolyte 308 in the sample chamber of nanopore cell 300. As examples, template 332 can be circular or linear. A nucleic acid primer can be hybridized to a portion of template 332 to which four differently polymer-tagged nucleotides 338 can be added.

In some embodiments, an enzyme (e.g., a polymerase 334, such as a DNA polymerase) is associated with nanopore 316 for use in the synthesizing a complementary strand to template 332. For example, polymerase 334 can be covalently attached to nanopore 316. Polymerase 334 can catalyze the incorporation of nucleotides 338 onto the primer using a single stranded nucleic acid molecule as the template. Nucleotides 338 can comprise tag species ("tags") with the nucleotide being one of four different types: A, T, G, or C. When a tagged nucleotide is correctly complexed with polymerase 334, the tag can be pulled (e.g., loaded) into the nanopore by an electrical force, such as a force generated in the presence of an electric field generated by a voltage applied across lipid bilayer 314 and/or nanopore 316. The tail of the tag can be positioned in the barrel of nanopore 316. The tag held in the barrel of nanopore 316 can generate a unique ionic blockade signal 340 due to the tag's distinct chemical structure and/or size, thereby electronically identifying the added base to which the tag attaches.

As used herein, a "loaded" or "threaded" tag is one that is positioned in and/or remains in or near the nanopore for an appreciable amount of time, e.g., 0.1 millisecond (ms) to 10000 ms. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 is high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase can then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule can also pass through the nanopore. These non-paired nucleotides can be rejected by the polymerase within a time scale that is shorter than the time scale for which correctly paired nucleotides remain associated with the polymerase. Tags bound to non-paired nucleotides can pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides can be identified by a downstream processor based at least in part on the time for which the nucleotide is detected in the nanopore.

A conductance (or equivalently the resistance) of the nanopore including the loaded (threaded) tag can be measured via a signal value (e.g., voltage or a current passing through the nanopore), thereby providing an identification of the tag species and thus the nucleotide at the current position. In some embodiments, a direct current (DC) signal is applied to the nanopore cell (e.g., so that the direction in which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode can deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement can be carried out with a voltage applied across the membrane and pore. In some embodiments, the voltage used ranges from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used can be more preferably in the range from 100 mV to 240 mV and most preferably in the range from 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-glycerol nucleoside triphosphates (gNTPs) of the five common nucleobases: adenine, cytosine, guanine, uracil, and thymine (Horhota et al., Organic Letters, 8:5345-5347 [2006]).

C. Electric Circuit of Nanopore Sequencing Cell

Figure 4:
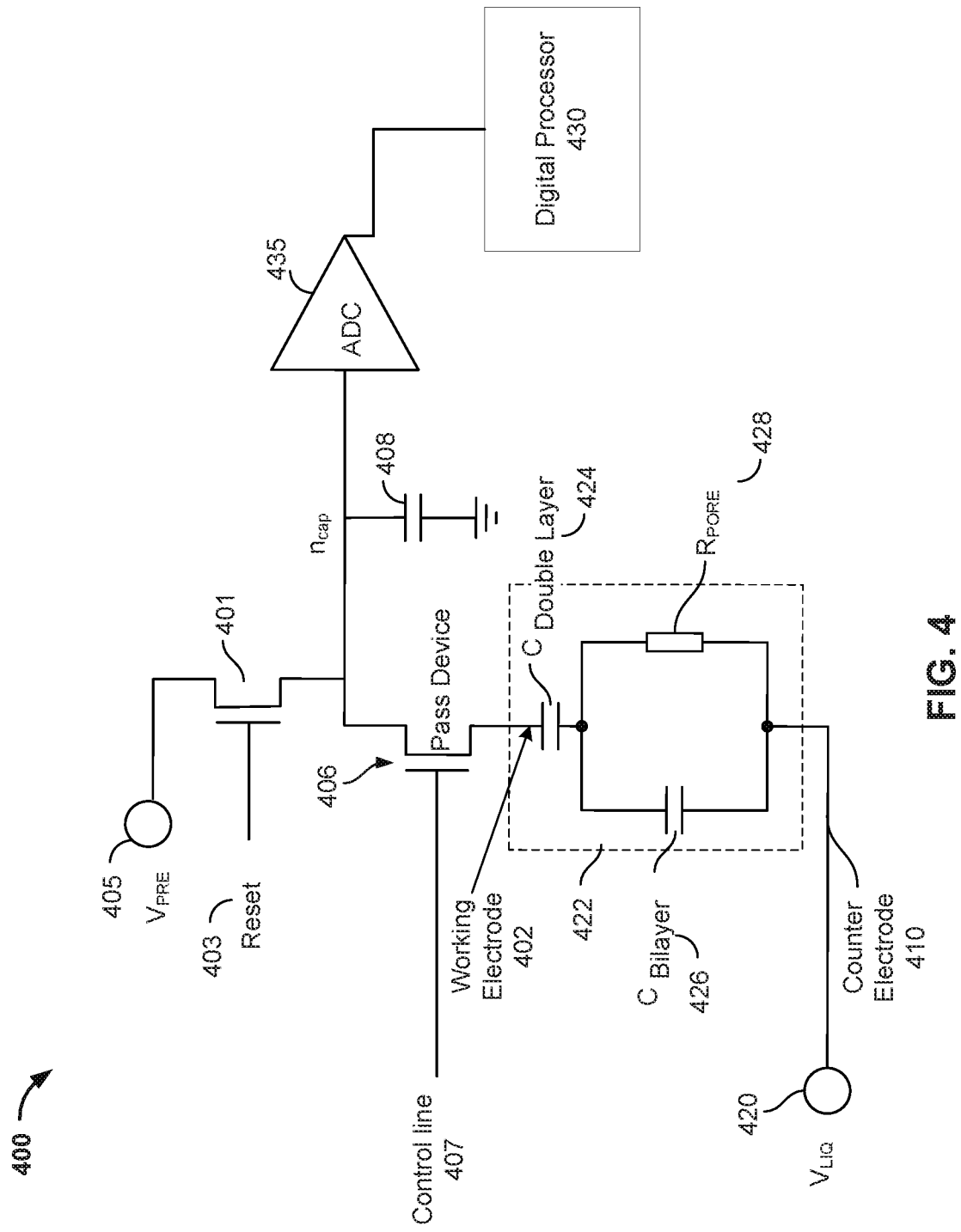
FIG. 4 illustrates an embodiment of an electric circuit in a nanopore cell.

FIG. 4 illustrates an embodiment of an electric circuit 400 (which may include portions of electric circuit 222 in FIG. 2) in a nanopore cell, such as nanopore cell 400. As described above, in some embodiments, electric circuit 400 includes a counter electrode 410 that can be shared between a plurality of nanopore cells or all nanopore cells in a nanopore sensor chip, and can therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a voltage source $V_{LIQ}$ 420. In some embodiments, an AC non-Faradaic mode is utilized to modulate voltage $V_{LIQ}$ with an AC signal (e.g., a square wave) and apply it to the bulk electrolyte in contact with the lipid bilayer in the nanopore cell. In some embodiments, $V_{LIQ}$ is a square wave with a magnitude of ±200-250 mV and a frequency between, for example, 25 and 400 Hz. The bulk electrolyte between counter electrode 410 and the lipid bilayer (e.g., lipid bilayer 214) can be modeled by a large capacitor (not shown), such as, for example, 100 μF or larger.

FIG. 4 also shows an electrical model 422 representing the electrical properties of a working electrode 402 (e.g., working electrode 202) and the lipid bilayer (e.g., lipid bilayer 214). Electrical model 422 includes a capacitor 426 ($C_{Bilayer}$) that models a capacitance associated with the lipid bilayer and a resistor 428 ($R_{PORE}$) that models a variable resistance associated with the nanopore, which can change based on the presence of a particular tag in the nanopore. Electrical model 422 also includes a capacitor 424 having a double layer capacitance ($C_{Double\ Layer}$) and representing the electrical properties of working electrode 402 and well 205. Working electrode 402 can be configured to apply a distinct potential independent from the working electrodes in other nanopore cells.

Pass device 406 is a switch that can be used to connect or disconnect the lipid bilayer and the working electrode from electric circuit 400. Pass device 406 can be controlled by control line 407 to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 406 can be kept open to avoid a short-circuit condition. Pass device 406 can be closed after lipid solvent has been deposited to the nanopore cell to seal the well of the nanopore cell.

Circuitry 400 can further include an on-chip integrating capacitor 408 ($n_{cap}$). Integrating capacitor 408 can be pre-charged by using a reset signal 403 to close switch 401, such that integrating capacitor 408 is connected to a voltage source $V_{PRE}$ 405. In some embodiments, voltage source $V_{PRE}$ 405 provides a constant reference voltage with a magnitude of, for example, 900 mV. When switch 401 is closed, integrating capacitor 408 can be pre-charged to the reference voltage level of voltage source $V_{PRE}$ 405.

After integrating capacitor 408 is pre-charged, reset signal 403 can be used to open switch 401 such that integrating capacitor 408 is disconnected from voltage source $V_{PRE}$ 405. At this point, depending on the level of voltage source $V_{LIQ}$, the potential of counter electrode 410 can be at a higher level than that of the potential of working electrode 402 (and integrating capacitor 408), or vice versa. For example, during a positive phase of a square wave from voltage source $V_{LIQ}$ (e.g., the bright or dark period of the AC voltage source signal cycle), the potential of counter electrode 410 is at a level higher than the potential of working electrode 402. During a negative phase of the square wave from voltage source $V_{LIQ}$ (e.g., the dark or bright period of the AC voltage source signal cycle), the potential of counter electrode 410 is at a lower level than that of the potential of working electrode 402. Thus, in some embodiments, integrating capacitor 408 can be further charged during the bright period from the pre-charged voltage level of voltage source $V_{PRE}$ 405 to a higher level, and discharged during the dark period to a lower level, due to the potential difference between counter electrode 410 and working electrode 402. In other embodiments, the charging and discharging occur in dark periods and bright periods, respectively.

Integrating capacitor 408 can be charged or discharged for a fixed period of time, depending on the sampling rate of an analog-to-digital converter (ADC) 435, which can be higher than 1 kHz, 5 kHz, 10 kHz, 100 kHz, or more. For example, with a sampling rate of 1 kHz, integrating capacitor 408 can be charged/discharged for a period of about 1 ms, and then the voltage level can be sampled and converted by ADC 435 at the end of the integration period. A particular voltage level would correspond to a particular tag species in the nanopore, and thus correspond to the nucleotide at a current position on the template.

After being sampled by ADC 435, integrating capacitor 408 can be pre-charged again by using reset signal 403 to close switch 401, such that integrating capacitor 408 is connected to voltage source $V_{PRE}$ 405 again. The steps of pre-charging integrating capacitor 408, waiting for a fixed period of time for integrating capacitor 408 to charge or discharge, and sampling and converting the voltage level of integrating capacitor by ADC 435 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 performs further downstream processing, such as base determination. Digital processor 430 can be implemented as hardware (e.g., in a graphics processing unit (GPU), FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore, also referred to herein as the unthreaded state of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor 408 is measured after a fixed period of time, the different states of a nanopore can result in measurements of different voltage levels. This is because the rate of the voltage decay (decrease by discharging or increase by charging) on integrating capacitor 408 (i.e., the steepness of the slope of a voltage on integrating capacitor 408 versus time plot) depends on the nanopore resistance (e.g., the resistance of resistor $R_{PORE}$ 428). More particularly, as the resistance associated with the nanopore in different states is different due to the molecules' (tags') distinct chemical structures, different corresponding rates of voltage decay can be observed and can be used to identify the different states of the nanopore. The voltage decay curve can be an exponential curve with an RC time constant $\tau=RC$, where R is the resistance associated with the nanopore (i.e., $R_{PORE}$ resistor 428) and C is the capacitance associated with the membrane (i.e., $C_{Bilayer}$ capacitor 426) in parallel with R. A time constant of the nanopore cell can be, for example, about 200-500 ms. The decay curve may not fit exactly to an exponential curve due to the detailed implementation of the bilayer, but the decay curve can be similar to an exponential curve and be monotonic, thus allowing detection of tags.

In some embodiments, the resistance associated with the nanopore in an open-channel state is in the range of 100 MOhm to 20 GOhm. In some embodiments, the resistance associated with the nanopore in a state where a tag is inside the barrel of the nanopore can be within the range of 200 MOhm to 40 GOhm. In other embodiments, integrating capacitor 408 is omitted, as the voltage leading to ADC 435 will still vary due to the voltage decay in electrical model 422.

The rate of the decay of the voltage on integrating capacitor 408 can be determined in different ways. As explained above, the rate of the voltage decay can be determined by measuring a voltage decay during a fixed time interval. For example, the voltage on integrating capacitor 408 can be first measured by ADC 435 at time $t_1$, and then the voltage is measured again by ADC 435 at time $t_2$. The voltage difference is greater when the slope of the voltage on integrating capacitor 408 versus time curve is steeper, and the voltage difference is smaller when the slope of the voltage curve is less steep. Thus, the voltage difference can be used as a metric for determining the rate of the decay of the voltage on integrating capacitor 408, and thus the state of the nanopore cell.

In other embodiments, the rate of the voltage decay is determined by measuring a time duration that is required for a selected amount of voltage decay. For example, the time required for the voltage to drop or increase from a first voltage level V1 to a second voltage level V2 can be measured. The time required is less when the slope of the voltage vs. time curve is steeper, and the time required is greater when the slope of the voltage vs. time curve is less steep. Thus, the measured time required can be used as a metric for determining the rate of the decay of the voltage on integrating capacitor $n_{cap}$ 408, and thus the state of the nanopore cell. One skilled in the art will appreciate the various circuits that can be used to measure the resistance of the nanopore, e.g., including signal value measurement techniques, such as voltage or current measurements.

In some embodiments, electric circuit 400 does not include a pass device (e.g., pass device 406) and an extra capacitor (e.g., integrating capacitor 408 ($n_{cap}$)) that are fabricated on-chip, thereby facilitating the reduction in size of the nanopore based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 can be used as the integrating capacitor, and can be pre-charged by the voltage signal $V_{PRE}$ and subsequently be discharged or charged by the voltage signal $V_{LIQ}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data Sampling in Nanopore Cell

To perform sequencing of a nucleic acid, the voltage level of integrating capacitor (e.g., integrating capacitor 408 ($n_{cap}$) or capacitor 426 ($C_{Bilayer}$)) can be sampled and converted by the ADC (e.g., ADC 435) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{LIQ}$ is lower than $V_{PRE}$.

1. Threading

A threading event is when a tagged nucleotide is attached to the template (e.g., nucleic acid fragment), and the tag moves in and out of the barrel of the nanopore. This movement can happen multiple times during a threading event. When the tag is in the barrel of the nanopore, the resistance of the nanopore can be higher, and a lower current can flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Period

During an AC cycle, the voltage on integrating capacitor can be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform can be referred to as a set. In a set of data points for an AC cycle, there can be a subset captured when, for example, $V_{LIQ}$ is lower than $V_{PRE}$, which can correspond to a bright mode (period) when the tag is forced into the barrel of the nanopore. Another subset can correspond to a dark mode (period) when the tag is pushed out of the barrel of the nanopore by the applied electric field when, for example, $V_{LIQ}$ is higher than $V_{PRE}$.

3. Measured Voltages

For each data point, when the switch 401 is opened, the voltage at the integrating capacitor (e.g., integrating capacitor 408 ($n_{cap}$) or capacitor 426 ($C_{Bilayer}$)) will change in a decaying manner as a result of the charging/discharging by $V_{LIQ}$, e.g., as an increase from $V_{PRE}$ to $V_{LIQ}$ when $V_{LIQ}$ is higher than $V_{PRE}$ or a decrease from $V_{PRE}$ to $V_{LIQ}$ when $V_{LIQ}$ is lower than $V_{PRE}$. The final voltage values can deviate from $V_{LIQ}$ as the working electrode charges. The rate of change of the voltage level on the integrating capacitor can be governed by the value of the resistance of the bilayer, which can include the nanopore, which can in turn include a molecule (e.g., a tag of a tagged nucleotides) in the nanopore. The voltage level can be measured at a predetermined time after switch 401 opens.

Switch 401 can operate at the rate of data acquisition. Switch 401 can be closed for a relatively short time period between two acquisitions of data, typically right after a measurement by the ADC. The switch allows multiple data points to be collected during each sub-period (bright or dark) of each AC cycle of $V_{LIQ}$. If switch 401 remains open, the voltage level on the integrating capacitor, and thus the output value of the ADC, fully decays and stays there. If instead switch 401 is closed, the integrating capacitor is precharged again (to $V_{PRE}$) and becomes ready for another measurement. Thus, switch 401 allows multiple data points to be collected for each sub-period (bright or dark) of each AC cycle. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information can allow the determination of how long a threading takes place. This can also be used in helping to determine whether multiple nucleotides that are added to the nucleic acid strand are being sequenced.

Figure 5:
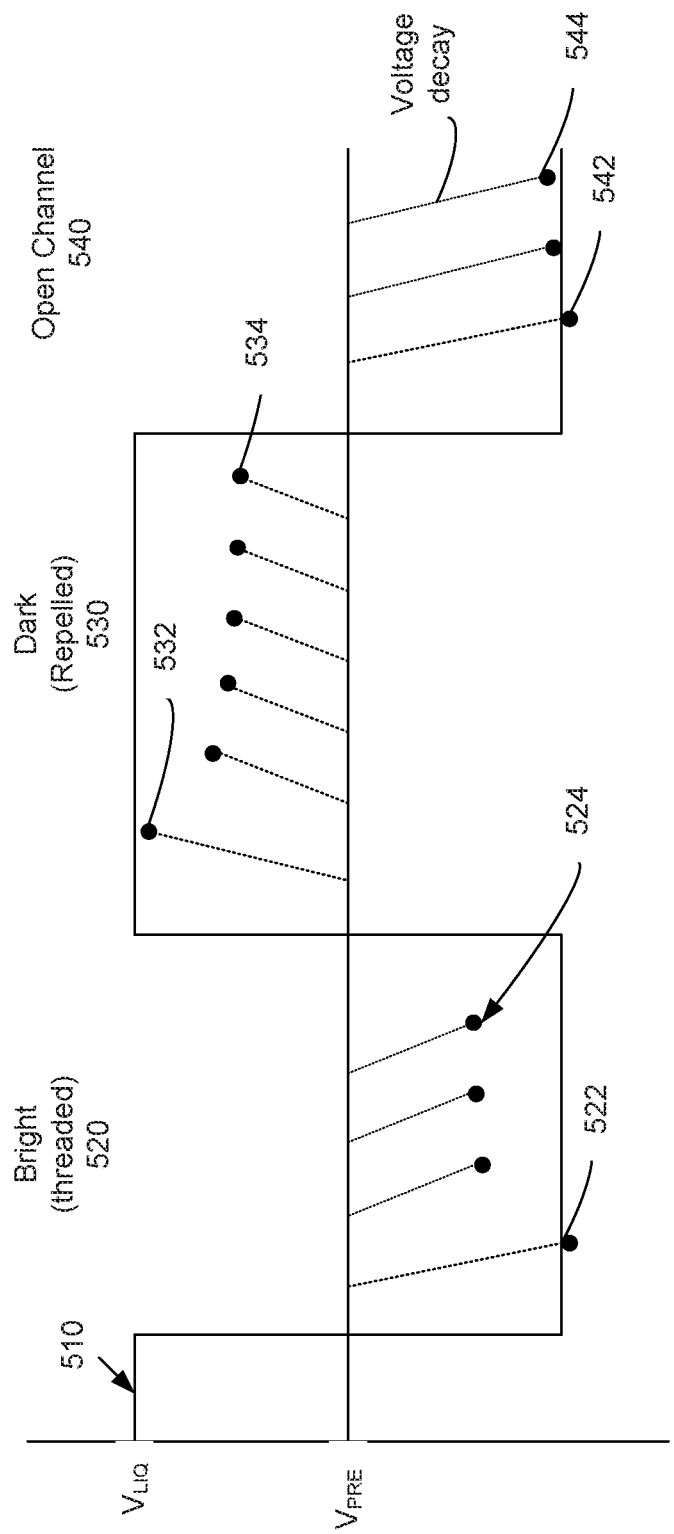
FIG. 5 shows example data points captured from a nanopore cell during bright periods and dark periods of AC cycles.

FIG. 5 shows example data points captured from a nanopore cell during bright periods and dark periods of AC cycles. In FIG. 5, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle can be any suitable value, such as less than or equal to 50%, for example, about 40%.

During a bright period 520, voltage signal 510 ($V_{LIQ}$) applied to the counter electrode is lower than the voltage $V_{PRE}$ applied to the working electrode, such that a tag can be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integrating capacitor) will decrease. After a voltage data point is captured (e.g., after a specified time period), switch 401 can be closed and the voltage at the measurement node will increase back to $V_{PRE}$ again. The process can repeat to measure multiple voltage data points. In this way, multiple data points can be captured during the bright period.

As shown in FIG. 5, a first data point 522 (also referred to as first point delta (FPD)) in the bright period after a change in the sign of the $V_{LIQ}$ signal can be lower than subsequent data points 524. This can be because there is no tag in the nanopore (open channel), and thus it has a low resistance and a high discharge rate. In some instances, first data point 522 can exceed the $V_{LIQ}$ level as shown in FIG. 5. This can be caused by the capacitance of the bilayer coupling the signal to the on-chip capacitor. Data points 524 can be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 524 can decrease slightly for each measurement due to charge built up at $C_{Double\ Layer}$ 424, as mentioned below.

During a dark period 530, voltage signal 510 ($V_{LIQ}$) applied to the counter electrode is higher than the voltage ($V_{PRE}$) applied to the working electrode, such that any tag would be pushed out of the barrel of the nanopore. When switch 401 is opened, the voltage at the measurement node increases because the voltage level of voltage signal 510 ($V_{LIQ}$) is higher than $V_{PRE}$. After a voltage data point is captured (e.g., after a specified time period), switch 401 can be closed and the voltage at the measurement node will decrease back to $V_{PRE}$ again. The process can repeat to measure multiple voltage data points. Thus, multiple data points can be captured during the dark period, including a first point delta 532 and subsequent data points 534. As described above, during the dark period, any nucleotide tag is pushed out of the nanopore, and thus minimal information about any nucleotide tag is obtained, besides for use in normalization.

FIG. 5 also shows that during bright period 540, even though voltage signal 510 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 424 ($C_{Double\ Layer}$). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5.

Further details regarding measurements can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation," the disclosures of which are incorporated by reference in their entirety for all purposes.

4. Normalization and Base Calling

For each usable nanopore cell of the nanopore sensor chip, a production mode can be run to sequence nucleic acids. The ADC output data captured during the sequencing can be normalized to provide greater accuracy. Normalization can account for offset effects, such as cycle shape, gain drift, charge injection offset, and baseline shift. In some implementations, the signal values of a bright period cycle corresponding to a threading event can be flattened so that a single signal value is obtained for the cycle (e.g., an average) or adjustments can be made to the measured signal to reduce the intra-cycle decay (a type of cycle shape effect). Gain drift generally scales entire signal and changes on the order to 100s to 1,000s of seconds. As examples, gain drift can be triggered by changes in solution (pore resistance) or changes in bilayer capacitance. The baseline shift occurs with a timescale of ~100 ms, and relates to a voltage offset at the working electrode. The baseline shift can be driven by changes in an effective rectification ratio from threading as a result of a need to maintain charge balance in the sequencing cell from the bright period to the dark period.

After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

III. Removing and Replacing Nanopores

As discussed above, each complex of a nanopore and associated template can be used to provide sequence information for a particular nucleic acid molecule of interest. To sequence an additional different molecule with the same array of cells, the nanopore complexes of the sequencing chip can be replaced. One method for accomplishing this involves the destruction of the membranes of each cell, so that nanopores within them can be removed from the chip, new membranes can be formed, and replacement nanopore complexes can be inserted in the new membranes. These steps add complexity to the sequencing process, however, and significantly impact the throughput and efficiency of the device and method.

An alternative process described herein involves the non-destructive manipulation of the lipid bilayer membranes within a sequencing chip. It has been found that by controlling the relative osmolarities on either side of a semipermeable lipid bilayer membrane, an osmotic flow of water across the membrane can be created. This water flow, and the resulting changes to the volumes of the reservoirs adjacent to the membrane, cause the membrane to change shape from a substantially planar configuration to one that is, for example, bowed inward. The bilayer nature of the membrane can be lost as the membrane bows inward and thickens, and this loss of the bilayer can introduce instability to the positioning of a protein pore within the membrane. Therefore, by introducing an osmotic imbalance across the membrane and causing the membrane to change shape, a nanopore within the membrane can be removed from the membrane by spontaneous ejection, without causing the membrane to lose structural integrity. By subsequently restoring the osmotic balance, the membrane can return to its original substantially planar shape and bilayer configuration. This bilayer configuration is then again conducive to protein pore stability, and a replacement nanopore can be passively or actively inserted therein.

A. Illustration of Nanopore Replacement

FIG. 6A illustrates a planar lipid bilayer membrane 601 spanning across a well 602 of a cell of a nanopore based sequencing chip. An initial nanopore 603 is inserted into the lipid bilayer. The bilayer separates the well from an external reservoir 604. At initial time $t_1$, the osmolarity [$E_W$] of the salt/electrolyte solution within the well is substantially identical to the osmolarity [$E_R$] of the external reservoir. In other implementations, the two osmolarities may be different, but not sufficiently different to eject initial nanopore 603.

FIG. 6B illustrates the cell at a later time $t_2$, at which a first electrolyte solution is flowed into the external reservoir. The first electrolyte solution has an osmolarity [$E_{S1}$] that is greater than the initial external reservoir osmolarity $[E_R]$ and the well osmolarity $[E_W]$. Because the flowing of the first electrolyte solution will increase the osmolarity of the external reservoir, an osmotic imbalance is introduced between the solutions on opposite sides of the lipid bilayer membrane. This imbalance provides a driving force for osmosis, in which water diffuses across the membrane from the well to the reservoir to equilibrate the well and reservoir osmolyte concentrations.

FIG. 6C illustrates the cell at a later time $t_3$, at which the osmotic diffusion of water has caused the liquid volume within the well to decrease. This change in volume creates a strain on the lipid bilayer membrane 601, causing the membrane to change its shape by bowing inward towards the well. The inward movement can result in the membrane thickening to a degree at which it is no longer a lipid bilayer in at least some portions spanning the well. This can in turn cause the initial nanopore 603 to be lost from the membrane, with the pore being ejected into the external reservoir as shown in FIG. 6C. After ejection, the initial nanopore generally diffuses into the larger volume of the external reservoir, such that it is no longer in proximity to the cell.

FIG. 6D illustrates the cell at later time $t_4$, at which a second electrolyte solution is flowed into the external reservoir. The second electrolyte solution can contain a plurality of replacement nanopores 605. In some implementations, an intermediate solution can be flowed, which does not contain replacement nanopore, but which can reduce the bowing in the membrane.

The concentration of replacement nanopores in the second electrolyte solution can be high enough that there is a significantly greater likelihood that a replacement nanopore being in proximity to the cell, than that the initial nanopore will be in proximity to the cell. As shown, the second electrolyte solution has an osmolarity $[E_{S2}]$ that is less than the first electrolyte solution osmolarity $[E_{S1}]$. Because the flowing of the second electrolyte solution will decrease the osmolarity of the external reservoir, another osmotic imbalance is introduced between the solutions on opposite sides of the membrane. This second osmotic imbalance provides another driving force for osmosis, with water now diffusing in an opposite direction across the membrane from the reservoir into the well to equilibrate the well and reservoir electrolyte concentrations.

FIG. 6E illustrates the cell at a later time $t_5$, at which the osmotic diffusion of water has caused the liquid volume within the well to increase. This change in volume of the well relieves the previous strain on the membrane, allowing the membrane to restore to its original planar shape spanning the well. The movement can result in the membrane again becoming a lipid bilayer at all or most positions across the well, thereby permitting nanopores to again become inserted into the membrane.

FIG. 6F illustrates the cell at a later time $t_6$, at which a replacement nanopore has been inserted into the planar lipid bilayer membrane spanning the well. The insertion of the nanopore into the membrane can be passive, or can be active. An active example, the insertion can be induced through the application of an electroporation voltage across the membrane.

B. Process for Nanopore Replacement

Figure 7:
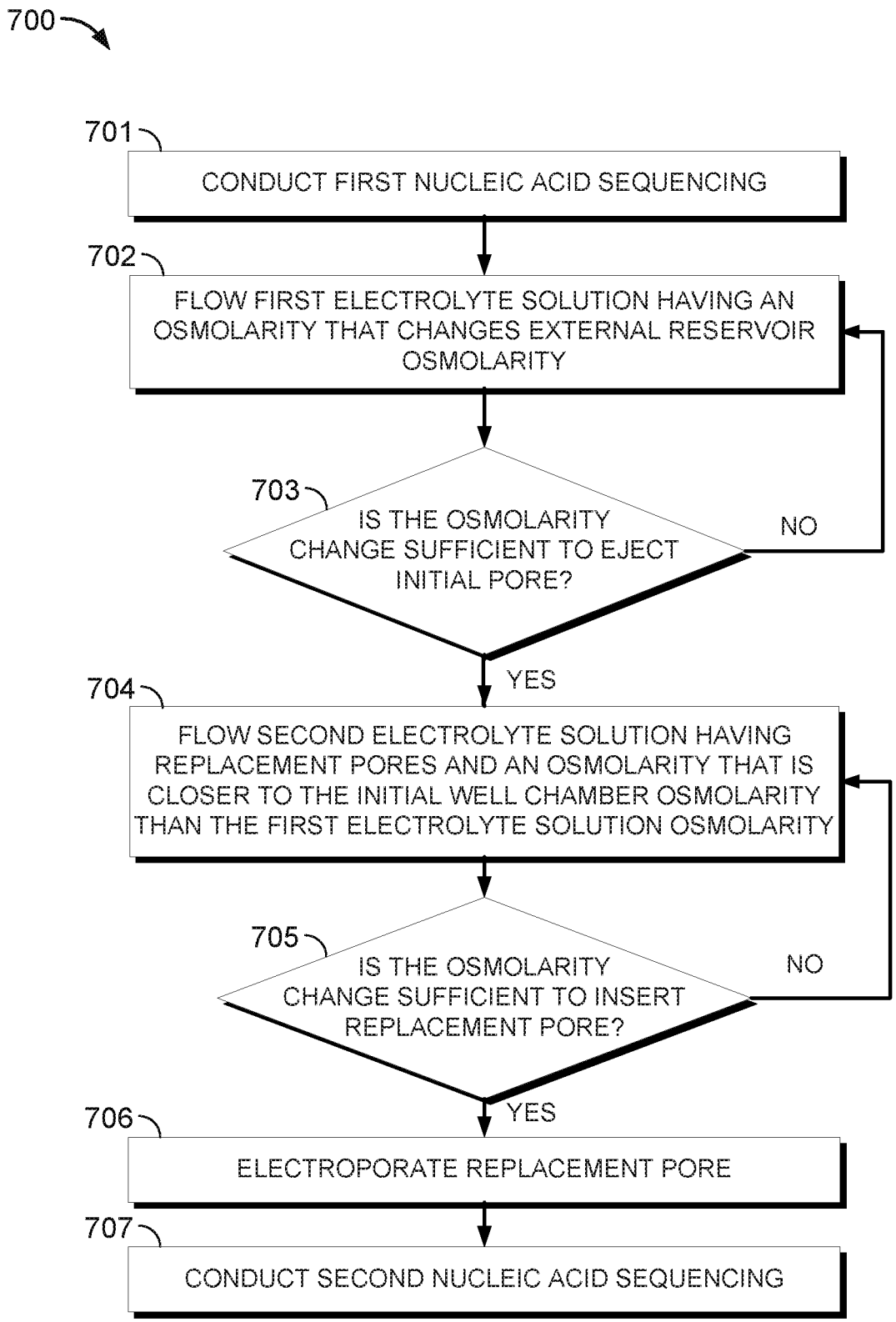
FIG. 7 is a flowchart of a process for replacing a nanopore in a membrane in accordance with an embodiment.

FIG. 7 illustrates an embodiment of a process 700 for replacing a nanopore inserted in a lipid bilayer in a cell of a nanopore based sequencing chip for analyzing molecules. The improved technique applies a first electrolyte flow over the planar lipid bilayer membrane, wherein the electrolyte flow has a different osmolarity than the osmolarity of the electrolyte solution below the planar lipid bilayer (i.e, within the well of the cell). The first electrolyte flow promotes the ejection of an initial nanopore or nanopore complex from the membrane. The technique further applies a second electrolyte flow over the membrane, wherein the electrolyte flow has an osmolarity that is similar or identical to the osmolarity of the electrolyte solution below the membrane. The second electrolyte flow can also contain a plurality of replacement nanopores, and the flowing of the second electrolyte solution can promote the insertion of a replacement nanopore into the planar lipid bilayer membrane.

The disclosed technique has many advantages, including the enabling of increased throughput of analyte to be sequenced. It is also appreciated that the disclosed technique can be applied to other semi-permeable membranes (e.g., other than a lipid bilayer) that permit the transmembrane flow of water but have limited to no permeability to the flow of ions or other osmolytes. For example, the disclosed methods and systems can be used with membranes that are polymeric. In some embodiments, the membrane is a copolymer. In some embodiments, the membrane is a triblock copolymer. It is also appreciated that the disclosed technique can be applied to membranes that are not elements of a nanopore based sequencing chip.

In some embodiments, the membrane is an element of a nanopore based sequencing chip. In some embodiments, a nanopore based sequencing chip 100 as shown in FIG. 1 is used for the process of FIG. 7. In some embodiments, the nanopore based sequencing chip used for the process of FIG. 7 includes a plurality of cells 200 of FIG. 2.

In optional step 701, nucleic acid sequencing is conducted. The sequencing can be performed with the data sampling methods and techniques described above. In some embodiments, the nucleic acid sequencing is performed with an electrical system as modeled in FIG. 4 used to detect nanopore states corresponding to the threading of the four types of tag-attached polyphosphate nucleotides.

In step 702, a first electrolyte solution is flowed to the reservoir (i.e., a first electrolyte reservoir) external to the well of the cell. Prior to the flowing of the first electrolyte solution, the external reservoir typically has an osmolarity (i.e., a first initial osmolarity) that is identical or similar to the osmolarity (i.e., a second initial osmolarity) of the solution within the well chamber (i.e., a second electrolyte reservoir). The first electrolyte solution has a concentration of electrolyte, or osmolyte, that is different from the first or second electrolyte reservoirs. In one embodiment, the first electrolyte solution has an osmolarity that is greater than the osmolarity of the first electrolyte reservoir prior to the flowing. It is appreciated that in alternate embodiments, the first electrolyte solution has an osmolarity that is less than the osmolarity of the first electrolyte reservoir prior to the flowing. In either case, the flowing of the first electrolyte solution acts to change the osmolarity of the external reservoir from the first initial osmolarity to a new osmolarity that is different from the initial osmolarity.

Each of the first electrolyte reservoir, the second electrolyte reservoir, and first electrolyte solution can independently have one or more osmolytes. Two or more of the first and second electrolyte reservoirs and the first electrolyte solution can include similar or different osmolytes. Osmolytes for use in the present invention include, without limitation, ionic salts such as lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride (MnCl$_2$), and magnesium chloride (MgCl$_2$); polyols and sugars such as glycerol, erythritol, arabitol, sorbitol, mannitol, xylitol, mannisidomannitol, glycosyl glycerol, glucose, fructose, sucrose, trehalose, and isofluoroside; polymers such as dextrans, levans, and polyethylene glycol; and some amino acids and derivatives thereof such as glycine, alanine, alpha-alanine, arginine, proline, taurine, betaine, octopine, glutamate, sarcosine, y-aminobutyric acid, and trimethylamine N-oxide (TMAO) (see also e.g., Fisher et al. U.S. 20110053795, incorporated herein by reference in its entirety). In one embodiment, a solution comprises an osmolyte that is an ionic salt. Those of ordinary skill in the art will appreciate other compounds that are suitable osmolytes for use in the present invention. In another aspect, the present invention provides solutions comprising two or more different osmolytes.

The initial osmolarities of the first and second electrolyte reservoirs (i.e, the first and second initial osmolarities, respectively) can be, for example and without limitation, within the range from 100 mM to 1 M, e.g., from 100 mM to 400 mM, from 125 mM to 500 mM, from 160 mM to 625 mM, from 200 mM to 800 mM, or from 250 mM to 1 M. The first and second electrolyte reservoirs can have initial osmolarities within the range from 200 mM to 500 mM, e.g., from 200 mM to 350 mM, from 220 mM to 380 mM, from 240 mM to 420 mM, from 260 mM to 460 mM, or from 290 mM to 500 mM. In terms of lower limits, the first and second electrolyte reservoirs can have initial osmolarities that are greater than 100 mM, greater than 125 mM, greater than 160 mM, greater than 200 mM, greater than 250 mM, greater than 400 mM, greater than 500 mM, greater than 625 mM, or greater than 800 mM. In terms of upper limits, the initial osmolarities of the first and second electrolyte reservoirs can be less than 1 M, less than 800 mM, less than 625 mM, less than 500 mM, less than 400 mM, less than 250 mM, less than 200 mM, less than 160 mM, or less than 125 mM.

In one embodiment, the concentration of solution in the external reservoir is between about 10 nM and 3M. In another embodiment, the concentration of solution in the external reservoir is about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, 305 mM, about 310 mM, about 315 mM, about 320 mM, about 325 mM, about 330 mM, about 335 mM, about 340 mM, about 345 mM, about 350 mM, about 355 mM, about 360 mM, about 365 mM, about 370 mM, about 375 mM, about 380 mM, about 385 mM, about 390 mM, about 395 mM, about 400 mM, about 450 mM, about 500 mM, about 550 mM, about 600 mM, about 650 mM, about 700 mM, about 750 mM, about 800 mM, about 850 mM, about 900 mM, about 950 mM, about 1 M, about 1.25 M, about 1.5 M, about 1.75 M, about 2 M, about 2.25 M, about 2.5 M, about 2.75 M, or about 3 M. In another embodiment, the concentration of solution in the well is about 305 mM, about 310 mM, about 315 mM, about 320 mM, about 325 mM, about 330 mM, about 335 mM, about 340 mM, about 345 mM, about 350 mM, about 355 mM, about 360 mM, about 365 mM, about 370 mM, about 375 mM, about 380 mM, about 385 mM, about 390 mM, about 395 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1 M. In one additional embodiment, the concentration of solution in the external reservoir is about 300 mM and the concentration of solution in the well is selected from the group consisting of about 310 mM, about 320 mM, about 330 mM, about 340 mM, about 350 mM, about 360 mM, about 370 mM, about 380 mM, about 390 mM, or about 400 mM. In other embodiments, the concentration of solutions is selected from the group consisting of (i) 300 mM in the external reservoir and 310 mM in the well, (ii) 300 mM in the external reservoir and 320 mM in the well, (iii) 300 mM in the external reservoir and 330 mM in the well, (iv) 300 mM in the external reservoir and 340 mM in the well, (v) 300 mM in the external reservoir and 350 mM in the well, (vi) 300 mM in the external reservoir and 360 mM in the well, (vii) 300 mM in the external reservoir and 370 mM in the well, (viii) 300 mM in the external reservoir and 380 mM in the well, (ix) 300 mM in the external reservoir and 390 mM in the well, and (x) 300 mM in the external reservoir and 400 mM in the well.

The ratio of the first electrolyte solution osmolarity to the external reservoir osmolarity can be, for example and without limitation, within the range from 1.05 to 1.5, e.g., from 1.05 to 1.3, from 1.08 to 1.35, from 1.13 to 1.4, from 1.17 to 1.45, or from 1.21 to 1.5. The ratio of the first electrolyte solution osmolarity to the external reservoir osmolarity can be within the range from 1.12 to 1.4, e.g., from 1.12 to 1.28 from 1.15 to 1.31, from 1.17 to 1.34, from 1.2 to 1.37, or from 1.22 to 1.4. In terms of lower limits, the ratio of the first electrolyte solution osmolarity to the external reservoir osmolarity can be greater than 1.05, greater than 1.08, greater than 1.17, greater than 1.21, greater than 1.3, greater than 1.35, greater than 1.4, or greater than 1.45. In terms of upper limits, the ratio of the first electrolyte solution osmolarity to the external reservoir osmolarity can be less than 1.5, less than 1.45, less than 1.4, less than 1.35, less than 1.3, less than 1.21, less than 1.17, less than 1.13, or less than 1.08.

In optional step 703, it is determined whether the flowing of the first electrolyte solution should be continued or repeated. Different criteria can be used to make the determination in this step. In some embodiments, step 702 is to be performed a predetermined number of times, and step 703 compares the number of times that step 702 has been performed with the predetermined number. In some embodiments, step 702 is to be performed for a predetermined period of time, and step 703 compares the cumulative amount of time that step 702 has been performed with the predetermined time period. In some embodiments, a measurement is made of the osmolarity of the solution within the external reservoir, or of the osmolarity of an efflux leaving the external reservoir. If the external reservoir or efflux osmolarity has not reached a predetermined value, then step 702 can be repeated. In some embodiments, step 702 is repeated until the osmolarity of the solution within or exiting the external reservoir is within a predetermined percentage range of the osmolarity of the solution (i.e., the first electrolyte solution) entering the external reservoir.

The concentration of electrolytes in the first electrolyte solution can be identical, similar, or different for each iteration of step 702. Lower or higher concentrations of electrolytes can be applied for one or multiple additional cycles. For example, each time that step 702 is repeated, the concentration of the salt electrolyte solution can be progressively increased from an initial electrolyte concentration or solution osmolarity (i.e., the conditions for a first iteration of step 702) to a final electrolyte concentration or solution osmolarity (i.e., the conditions for a last iteration of step 702), until the $[E_{S1}]/[E_W]$ ratio is increased to a predetermined target ratio. This ratio can be estimated by using osmolarity measurements of the external reservoir fluid exiting the system. If the flowing of the electrolyte solution (in step 702) is repeated, process 700 can proceed to step 702 from step 703; otherwise, process 700 can proceed to step 704.

In step 704, a second electrolyte solution is flowed to the reservoir external to the well of the cell. The second electrolyte solution has a concentration of electrolyte, or osmolyte, that is different from that of electrolyte in the first electrolyte solution. The second electrolyte solution osmolarity is also closer to the second initial osmolarity (i.e., the initial osmolarity of the electrolyte solution in the well chamber) than the first electrolyte solution osmolarity. In other words, the difference between the second electrolyte solution osmolarity and the second initial osmolarity is less than the difference between the first electrolyte solution osmolarity and the second initial osmolarity. In one embodiment, the second electrolyte solution has an osmolarity that is less than the osmolarity of the first electrolyte solution. It is appreciated that in alternate embodiments, the second electrolyte solution has an osmolarity that is greater than osmolarity of the first electrolyte solution. In either case, the flowing of the second electrolyte solution acts to change the osmolarity of the external reservoir, such that the external reservoir osmolarity becomes closer to the initial well reservoir osmolarity. The second electrolyte solution can have one or more osmolytes, each of which can independently be any of the osmolytes described above.

The second electrolyte solution can include a plurality of replacement nanopores. Each of the plurality of replacement nanopores can be a part of one of a plurality of replacement nanopore complexes. The replacement nanopore complexes can include, for example, a polymerase and a template. The template of each replacement nanopore complex can be different from the template that was present in the initial nanopore complex being replaced. The initial and replacement nanopores, or the nanopores of the initial and replacement nanopore complexes, can each independently be, for example and without limitation, outer membrane protein G (OmpG); bacterial amyloid secretion channel CsgG; *Mycobacterium smegmatis* porin A (MspA); alpha-hemolysin (α-HL); any protein having at least 70% homology to at least one of OmpG, CsgG, MspA, or α-HL; or any combination thereof The ratio of the first electrolyte solution osmolarity to the second electrolyte solution osmolarity can be, for example and without limitation, within the range from 1.05 to 1.5, e.g., from 1.05 to 1.3, from 1.08 to 1.35, from 1.13 to 1.4, from 1.17 to 1.45, or from 1.21 to 1.5. The ratio of the first electrolyte solution osmolarity to the second electrolyte solution osmolarity can be within the range from 1.12 to 1.4, e.g., from 1.12 to 1.28 from 1.15 to 1.31, from 1.17 to 1.34, from 1.2 to 1.37, or from 1.22 to 1.4. In terms of lower limits, the ratio of the first electrolyte solution osmolarity to the second electrolyte solution osmolarity can be greater than 1.05, greater than 1.08, greater than 1.17, greater than 1.21, greater than 1.3, greater than 1.35, greater than 1.4, or greater than 1.45. In terms of upper limits, the ratio of the first electrolyte solution osmolarity to the second electrolyte solution osmolarity can be less than 1.5, less than 1.45, less than 1.4, less than 1.35, less than 1.3, less than 1.21, less than 1.17, less than 1.13, or less than 1.08.

The ratio of the second electrolyte solution osmolarity to the well solution osmolarity, or to the osmolarity of the external reservoir prior to the flowing of the first electrolyte solution in step 702 (i.e., the first initial osmolarity), can be, for example and without limitation, within the range from 0.85 to 1.15, e.g., from 0.85 to 1.03, from 0.88 to 1.06, from 0.91 to 1.09, from 0.94 to 1.12, or from 0.97 to 1.15. The ratio of the second electrolyte solution osmolarity to the first initial osmolarity can be within the range from 0.94 to 1.06, e.g., from 0.94 to 1.02, from 0.95 to 1.03, from 0.96 to 1.04, from 0.97 to 1.05, or from 0.98 to 1.06. In terms of lower limits, the ratio of the second electrolyte solution osmolarity to the first initial osmolarity can be greater than 0.85, greater than 0.88, greater than 0.91, greater than 0.94, greater than 0.97, greater than 1, greater than 1.03, greater than 1.06, greater than 1.09, or greater than 1.12. In terms of upper limits, the ratio of the second electrolyte solution osmolarity to the first initial osmolarity can be less than 1.15, less than 1.12, less than 1.09, less than 1.06, less than 1.03, less than 1, less than 0.97, less than 0.94, less than 0.91, or less than 0.88.

In optional step 705, it is determined whether the flowing of the second electrolyte solution should be continued or repeated. Different criteria can be used to make the determination in this step. In some embodiments, step 704 is performed a predetermined number of times, and step 705 compares the number of times that step 704 has been performed with the predetermined number. In some embodiments, step 704 is to be performed for a predetermined period of time, and step 705 compares the cumulative amount of time that step 704 has been performed with the predetermined time period. In some embodiments, a measurement is made of the osmolarity of the solution within the external reservoir, or of the osmolarity of an efflux leaving the external reservoir. If the external reservoir or efflux osmolarity has not reached a predetermined value, then step 704 can be repeated. In some embodiments, step 704 is repeated until the osmolarity of the solution within or exiting the external reservoir is within a predetermined percentage range of the osmolarity of the solution (i.e., the second electrolyte solution) entering the external reservoir. In some embodiments, step 704 is repeated until the osmolarity of the solution within or exiting the external reservoir is within a predetermined percentage range of the osmolarity of the solution (i.e., the second reservoir) within the well chamber.

The concentration of electrolytes in the first electrolyte solution can be identical, similar, or different for each iteration of step 704. Lower or higher concentrations of electrolytes can be applied for one or multiple additional cycles. For example, each time step 704 is repeated the concentration of the salt electrolyte solution can be progressively decreased from an initial electrolyte concentration or solution osmolarity (i.e., the conditions for a first iteration of step 704) to a final electrolyte concentration or solution osmolarity (i.e., the conditions for a last iteration of step 704), until the $[E_{S2}]/[E_W]$ ratio is decreased to a predetermined target ratio. This ratio can be estimated by using osmolarity measurements of the external reservoir fluid exiting the system. If the flowing of the electrolyte solution (in step 704) is repeated, process 700 can proceed to step 704 from step 705; otherwise, process 700 can proceed to step 706.

In optional step 706 of process 700, one of the plurality of replacement nanopores of the second electrolyte solution is inserted into the membrane of the cell. Different techniques can be used to insert nanopores in the cells of the nanopore based sequencing chip. In some embodiments, the nanopore inserts passively, i.e., without the use of an external stimulus. In some embodiments, an agitation or electrical stimulus (e.g., a voltage of 100 mV to 1.0 V for 50 milliseconds to 1 second) is applied across the lipid bilayer membrane, causing a disruption in the lipid bilayer and initiating the insertion of a nanopore into the lipid bilayer. In some embodiments, the voltage applied across the membrane is an alternating current (AC) voltage. In some embodiments, the voltage applied across the membrane is a direct current (DC) voltage. An electroporation voltage applied across the membrane of a cell can be generally applied to all cells of the nanopore based sequencing chip, or the voltage can be specifically targeted to one or more cells of the chip.

In optional step 707 of process 700, nucleic acid sequencing is conducted. The sequencing can be performed with the data sampling methods and techniques described above. In some embodiments, the template associated with the replacement nanopore complex inserted in step 706 is different from the template associated with the initial nanopore complexes ejected as a result of the first electrolyte solution flow of step 704. In this case, the sequencing operation of step 707 can be used to analyze a different nucleic acid sequence than was analyzed with the sequencing operation of step 701. This can increase the efficiency of the sequencing chip, allowing individual cells of the chip to be used in the sequencing of multiple different nucleic acid molecules due to the replacement of sequencing nanopores.

C. Flow System for Nanopore Replacement

Process 700 of FIG. 7 includes steps (e.g., steps 701, 702, 704, and 707) in which different types of fluids (e.g., liquids or gases) are flowed through a reservoir external to a well. Multiple fluids with significantly different properties (e.g., osmolarity, compressibility, hydrophobicity, and viscosity) can be flowed over an array of sensor cells (e.g., such as cell 200 of FIG. 2) on the surface of a nanopore based sequencing chip (e.g, such as chip 100 of FIG. 1). In some embodiments, a system that performs process 700 includes a flow system that directs and/or monitors the flow of different fluids into and out of the external reservoir.

Figure 8:
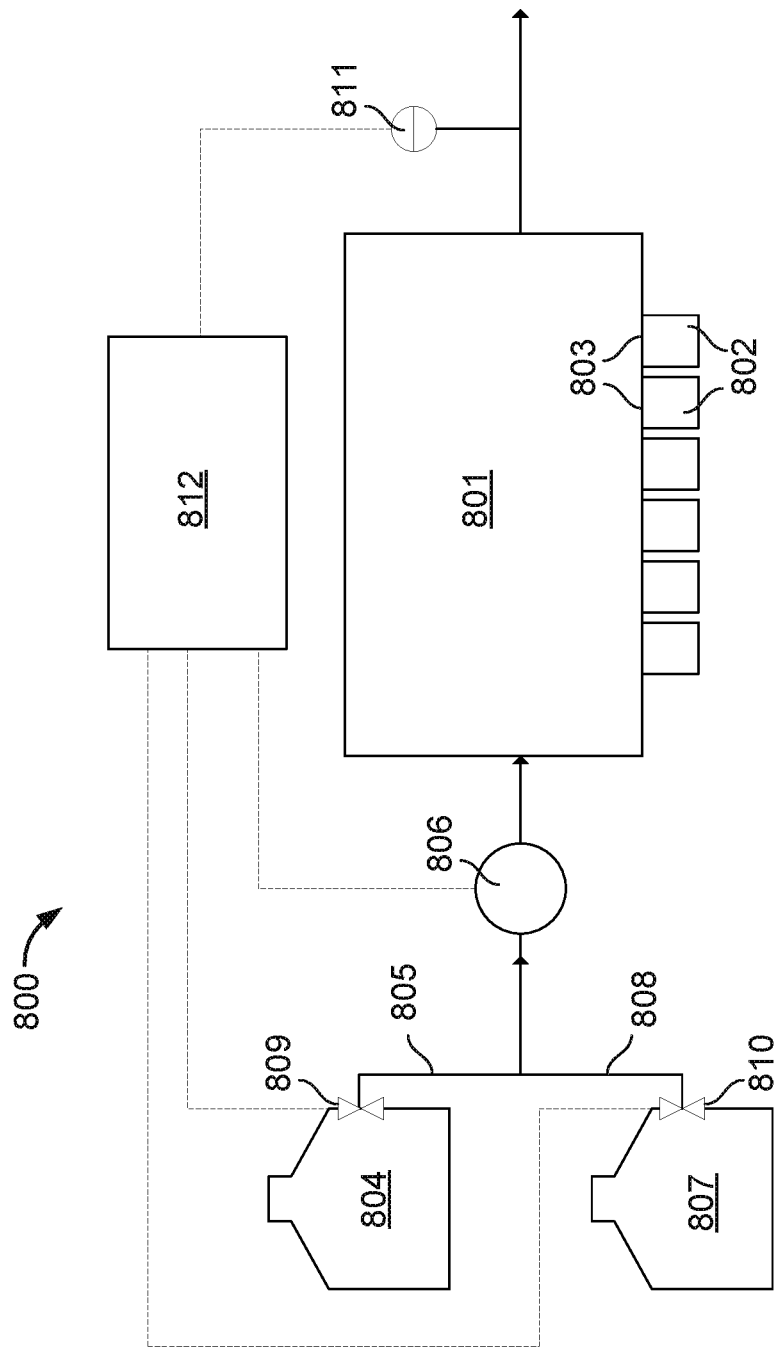
FIG. 8 is a flow system, according to certain aspects of the present disclosure.

FIG. 8 illustrates an embodiment of a flow system 800 for use with process 700 of FIG. 7. The flow system includes a first electrolyte reservoir 801 that is external to an array of wells 802. For each of the wells, the interior well chamber (i.e., a second electrolyte reservoir) can be divided from the first electrolyte reservoir by a membrane 803 that includes an inserted initial nanopore or nanopore complex. In step 701 of process 700, nucleic acid sequencing can be conducted using the flow system 800. As part of this nucleic acid sequencing, one or more fluids can be flowed into or through the first electrolyte reservoir 801. These one or more fluids can be initially held in one or more storage vessels (e.g., first storage vessel 804 of FIG. 8) external to the first electrolyte reservoir. Each of the one more storage vessels can independently or jointly be in fluidic connection with the first electrolyte reservoir through one or more channels, tubes, or pipes (e.g., first channel 805). The transfer of fluid from first storage vessel 804 through first channel 805 and into first electrolyte reservoir 801 can be with the action of one or more pumps (e.g., pump 806). Each pump can be, for example, a positive displacement pump or an impulse pump. Control circuitry 812 can be communicably coupled with pump 806, e.g., for sending a control signal to pump 806 for controlling the transfer of fluid from first storage vessel 804 through first channel 805 and into first electrolyte reservoir 801. Fluid can enter the first reservoir 801 across substantially the entire width of the first reservoir 801, or can enter the first reservoir 801 through a channel (e.g., a serpentine channel) that directs flow within the first electrolyte reservoir 801.

The flow system 800 can also include a second storage vessel 807 that can be used to hold the first electrolyte solution of step 702 of process 700. The second storage vessel 807 can be in fluidic connection with the first electrolyte reservoir through a channel, tube, or pipe (e.g., second channel 808). The transfer of fluid from second storage vessel 807 through second channel 808 and into first electrolyte reservoir 801 can be with the action of one or more pumps. One or more of the one or more pumps used to transfer fluid from second storage vessel 807 in step 702 can be the same as one or more pumps used to transfer fluid from the first storage vessel 804 in step 701. For example, and as shown in FIG. 8, a pump 806 can be used to pump fluid through a common shared portion of the first 805 and second 808 channels.

In some embodiments, one or more valves (e.g., valves 809 and 810) are used to control the fluid flow exiting one or more of the storage vessels. For example, as process 700 proceeds from step 701 to step 702, first valve 809 can be completely closed and second valve 807 can be opened, such that fluid flow associated with nucleic acid sequencing is stopped and flow of the first electrolyte solution is begun. As another example, as process 700 proceeds from step 701 to 702, the opening of first valve 809 can be narrowed and/or the opening of second valve 807 can be expanded, such that the ratio of fluids from storage vessels 804 and 807 entering first electrolyte reservoir 801 is adjusted. Control circuitry 812 can be communicably coupled with first valve 809 and second valve 810, e.g., for sending a control signal to first valve 809 and/or second valve 810 for adjusting the ratio of fluids from storage vessels 804 and 807 entering first electrolyte reservoir 801.

The flow system 800 can also include a detector 811 to monitor the osmolarity of fluid exiting the first electrolyte reservoir 801. In some embodiments, the detector 811 is communicably connected to control circuitry for monitoring fluid osmolarity and controlling electrolyte solution flow. In some embodiments, another detector (not shown) is located within the first electrolyte reservoir to measure the osmolarity of fluid within the first electrolyte reservoir. In other embodiments, the flow system does not have an osmolarity detector.

In step 703 of process 700, the detector 811 can be used to determine whether the flowing of the first electrolyte solution from storage vessel 807 into first electrolyte reservoir 801 should be continued or repeated. For example, the detector 811 can report an osmolarity measurement, and a comparison of this measurement with a preselected osmolarity value can be used to determine if process 700 proceeds to step 702 or step 704 from step 703. In some embodiments, if process 700 proceeds to step 702, then the first valve 809 and second valve 810 are controlled to adjust the ratio of fluids entering the first electrolyte reservoir 801 in the new step 702 iteration. For example, if the osmolarity of the first electrolyte solution within second storage vessel 807 is greater than the osmolarity of the solution within first storage vessel 804, then each time that step 702 is repeated, the opening of first valve 809 can be narrowed and/or the opening of second valve 807 can be expanded. In this way, the concentration of salt electrolyte solution entering first electrolyte reservoir 801 can be progressively increased from an initial electrolyte concentration or solution osmolarity (i.e., the conditions for a first iteration of step 702) to a final electrolyte concentration or solution osmolarity (i.e., the conditions for a last iteration of step 702), until the $[E_{801}]/[E_{802}]$ ratio is increased to a predetermined target ratio.

In some embodiments, the ratio of fluids from storage vessels 804 and 807 entering first electrolyte reservoir 801 is adjusted with the use of pumps instead of valves. For example, the flow rate of a pump transferring fluid from storage vessel 804 can be decreased and/or the flow rate of a pump transferring the first electrolyte solution from storage vessel 807 can be increased, so as to progressively increase the osmolarity within first electrolyte reservoir 801.

The second electrolyte solution flowed to the first electrolyte reservoir 801 in step 704 of process 700 can also be held in one or more storage vessels of flow system 800. In some embodiments, the second electrolyte solution is identical to the one or more fluids used during the nucleic acid sequencing of step 701 of process 700. In some embodiments, the second electrolyte solution is within first storage vessel 804. In some embodiments, the second electrolyte solution is within a storage vessel other than first 804 or second 807 storage vessels. The storage vessel of the second electrolyte solution can be in fluidic connection with the first reservoir through one or more of any of the channels, tubes, pipes, pumps, or valves of the types and configurations described above. In some embodiments, as process 700 proceeds from step 703 to step 704, first valve 809 is completely opened and second valve 810 is closed, such that flow of the first electrolyte solution is stopped and flow of the second electrolyte solution is begun. In some embodiments, as process 700 proceeds from step 703 to step 704, the opening of first valve 809 is expanded and/or the opening of second valve 807 is narrowed, such that the ratio of fluids from storage vessels 804 and 807 entering first electrolyte reservoir 801 is adjusted.

The detector 811 of flow system 800 can also be used in step 705 of process 700 to determine whether the flowing of the second electrolyte solution into first electrolyte reservoir 801 should be continued or repeated. For example, the detector 811 can report an osmolarity measurement, and a comparison of this measurement with a preselected osmolarity value can be used to determine if process 700 proceeds to step 704 or step 706 from step 705. In some embodiments, if process 700 proceeds to step 704, then the first 809 and second 810 valves are controlled to adjust the ratio of fluids entering the first electrolyte reservoir 801 in the new step 704 iteration. For example, if the osmolarity of the first electrolyte solution within second storage vessel 807 is greater than the osmolarity of the second electrolyte solution within first storage vessel 804, then each time that step 704 is repeated, the opening of first valve 809 can be expanded and/or the opening of second valve 807 can be narrowed.

In this way, the concentration of salt electrolyte solution entering first electrolyte reservoir 801 can be progressively decreased from an initial electrolyte concentration or solution osmolarity (i.e., the conditions for a first iteration of step 704) to a final electrolyte concentration or solution osmolarity (i.e., the conditions for a last iteration of step 704), until the $[E_{801}]/[E_{802}]$ ratio is decreased to a predetermined target ratio. In some embodiments, the ratio of fluids from storage vessels 804 and 807 entering first electrolyte reservoir 801 is adjusted with the use of pumps instead of valves. For example, the flow rate of a pump transferring the second electrolyte solution from storage vessel 804 can be increase and/or the flow rate of a pump transferring the first electrolyte solution from storage vessel 807 can be decreased, so as to progressively decrease the osmolarity within first electrolyte reservoir 801.

D. Example of Nanopore Replacement

Embodiments of the present invention will be better understood in view of the following non-limiting example.

Initial alpha-hemolysin nanopores were electroporated into the membranes of the cells of a sequencing chip with an external reservoir and a well reservoir, each containing a 380 mM potassium glutamate (KGlu) buffer. Streptavidin-bound oligo(dT)$_{40}$ tags were then flowed into the external reservoir in a 300 mM KGlu buffer. As a positive control, two independent measurements were taken of the free capture rate ($k_{fc}$) for each single pore cell in the chip. The free capture rate refers to the number of tag insertion events occurring per unit time for a given pore. The two measurements are taken at different times for a same cell, with no ejection or new insertion of a pore.

Figures 9A, 9B:
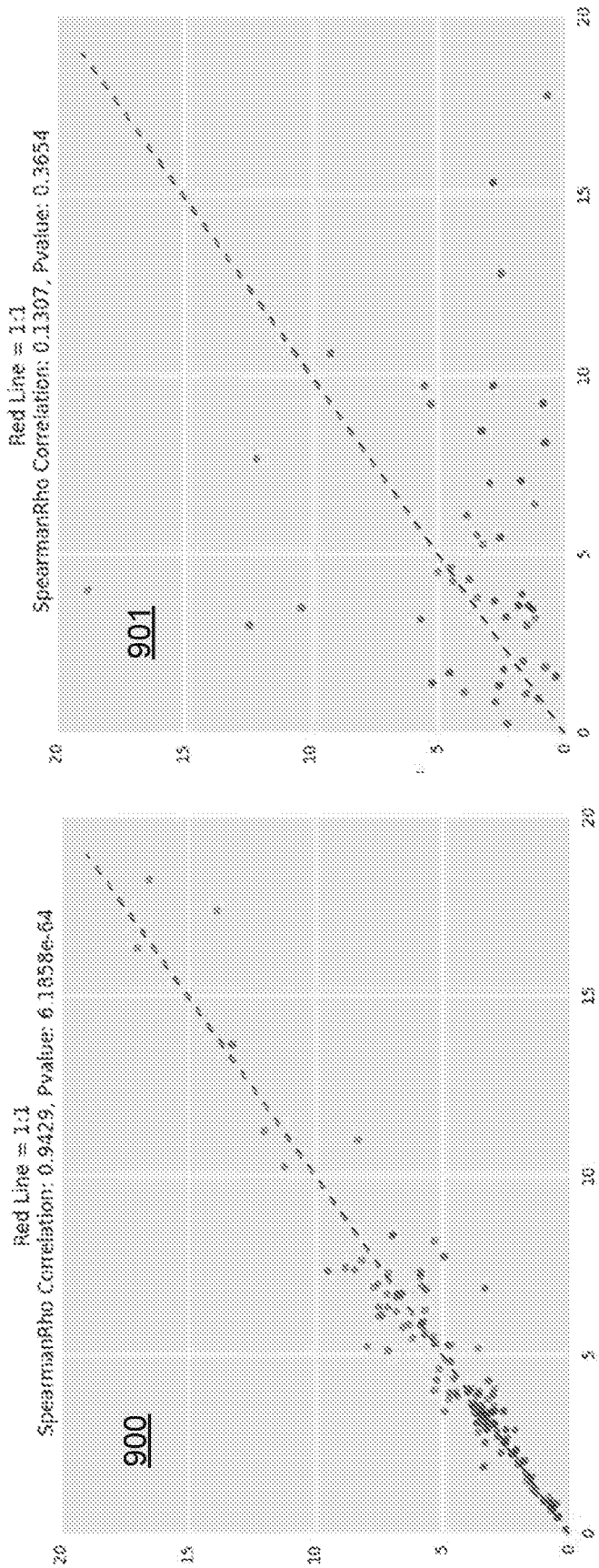
FIG. 9A is a graph plotting the relationship between two independent $k_{fc}$ value measurements for the cells of a nanopore based sequencing chip, without the application of a pore replacement method.
FIG. 9B is a graph plotting the relationship between two independent $k_{fc}$ value measurements for the cells of a nanopore based sequencing chip, with the application of a pore replacement method in accordance with an embodiment between the two measurements.

FIG. 9A shows a graph 900 plotting results from these measurements The x- and y-axes of the FIG. 9A graph indicate $k_{fc}$ measurement values, and each data point represents the relationship between the two measurements for an individual cell and nanopore. Because the pore is not changed between measurements, ideal results would produce points that all lie on the dashed y=x line. The small deviations of data point positions from this ideal line are indicative of standard experimental errors, such as, for example, data acquisition noise. As shown, the measurements do generally follow a line, which is in contrast with the measurements of cells that undergo a pore swap using embodiments of the present invention, as explained below.

A first electrolyte solution of 380 mM KGlu was then flowed into the external reservoir of the sequencing chip, followed by a second electrolyte solution of 300 mM KGlu. The second electrolyte solution contained replacement alpha-hemolysin nanopores, and replacement streptavidin-bound oligo(dT)$_{40}$ tags. The replacement nanopores were allowed to passively insert into the cell membranes of the chip, and to complex with the replacement tags to form replacement nanopore complexes. Another measurement was taken of the $k_{fc}$ for each cell in the chip, and these new measurements were compared with those taken before the flowing of the electrolyte solutions.

FIG. 9B shows a graph 901 plotting results from these measurements. The x- and y-axes again indicate $k_{fc}$ measurements, and each data point of FIG. 9B represents the relationship between measurements taken before and after the electrolyte solution flows for an individual cell. From the graph it can be seen that the average deviation of data point positions from the ideal y=x line is significantly greater for the FIG. 9B plot than for the FIG. 9A plot. This indicates that the cells have different properties after the flowing of the electrolyte solutions, and that these different properties are not caused by experimental or measurement error or noise, but are instead caused by the replacement of initial nanopores and nanopore complexes with replacement nanopores and nanopore complexes. Thus, FIGS. 9A and 9B shows that pores were ejected and new pores inserted using embodiments of the present invention.

The absence and presence of pore swapping events can also be demonstrated in data traces of ADC output, such as those of FIGS. 10A and 10B.

FIG. 10A shows a graph 1001 of ADC counts (plotted on the x-axis) over time (plotted on the y-axis) measured with a sequencing cell for which pore swapping was not induced. Seen in the graph are thick bands showing voltage measurements of the bright open channel 1002 and dark open channel 1003 outputs. At time 1004, a first electrolyte solution was flowed into the external reservoir of the sequencing cell, wherein the first electrolyte solution had a different osmolarity than the initial osmolarity of the external reservoir, but wherein the osmolarity difference was not great enough to promote ejection of the nanopore of the sequencing cell.

For times immediately after time 1004, the small osmotic imbalance between the new osmolarity of the external reservoir and the well reservoir of the sequencing cell caused a minor change in the configuration of the membrane of the sequencing cell. This minor change resulted in an increase in the separation 1005 between the bright open channel 1002 and dark open channel 1003 outputs. At time 1006, a second electrolyte solution was flowed into the external reservoir, wherein the second electrolyte solution had an osmolarity that was closer to the initial osmolarity of the well reservoir of the sequencing cell than the first electrolyte solution osmolarity. As a result of this second electrolyte solution flow, the separation 1005 between the bright open channel 1002 and dark open channel 1003 outputs was restored to an amount similar to that observed prior to time 1004.

FIG. 10B shows a graph 1011 of ADC counts over time measured with a sequencing cell for which pore swapping was induced. At time 1014, a first electrolyte solution was flowed into the external reservoir of the sequencing cell, wherein the first electrolyte solution had a different osmolarity than the initial osmolarity of the external reservoir, and wherein the osmolarity difference was great enough to promote ejection of the nanopore of the sequencing cell. For times immediately after time 1014, the nanopore ejection resulted in a collapse of the separation 1015 between the bright open channel 1012 and dark open channel 1013, wherein the lack of separation was indicative of the lack of an inserted nanopore.

At time 1016, a second electrolyte solution was flowed into the external reservoir, wherein the second electrolyte solution had an osmolarity that was closer to the initial osmolarity of the well reservoir of the sequencing cell than the first electrolyte solution. As a result of this second electrolyte solution flow, the configuration of the membrane of the sequencing cell was restored to its original configuration and was once again conducive to pore insertion. At time 1017, a replacement pore was inserted into the membrane, and the separation 1015 between the bright open channel 1012 and dark open channel 1013 outputs was reintroduced, wherein the separation was indicative of the presence of an inserted nanopore. Thus, FIG. 10B also shows in contrast with FIG. 10A that a pore were ejected and a new pore inserted using embodiments of the present invention.

IV. Computer System

Figure 11:
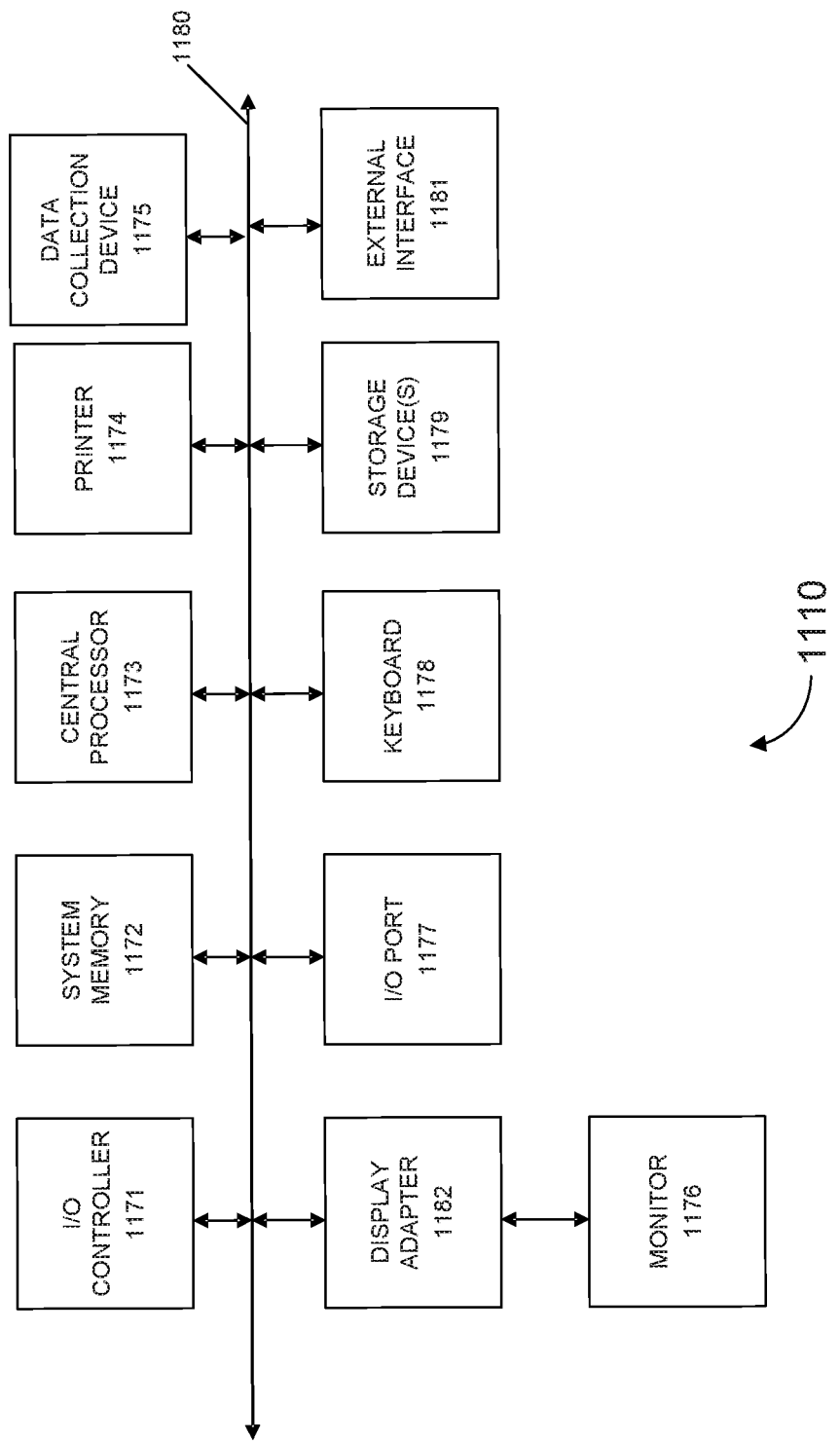
FIG. 11 is a computer system, according to certain aspects of the present disclosure.

Any of the computer systems mentioned herein can utilize any suitable number of subsystems. Examples of such subsystems are shown in FIG. 11 in computer system 1110. In some embodiments, a computer system includes a single computer apparatus, where the subsystems can be the components of the computer apparatus. In other embodiments, a computer system includes multiple computer apparatuses, each being a subsystem, with internal components. A computer system can include desktop and laptop computers, tablets, mobile phones, and other mobile devices.

The subsystems shown in FIG. 11 are interconnected via a system bus 1180. Additional subsystems such as a printer 1174, keyboard 1178, storage device(s) 1179, monitor 1176 which is coupled to display adapter 1182, and others are shown. Peripherals and input/output (I/O) devices, which couple to I/O controller 1171, can be connected to the computer system by any number of means known in the art such as I/O port 1177 (e.g., USB, FireWire®). For example, I/O port 1177 or external interface 1181 (e.g. Ethernet, Wi-Fi, etc.) can be used to connect computer system 1110 to a wide area network such as the Internet, a mouse input device, or a scanner. The interconnection via system bus 1180 allows the central processor 1173 to communicate with each subsystem and to control the execution of a plurality of instructions from system memory 1172 or the storage device(s) 1179 (e.g., a fixed disk, such as a hard drive, or optical disk), as well as the exchange of information between subsystems. The system memory 1172 and/or the storage device(s) 1179 can embody a computer readable medium. Another subsystem is a data collection device 1175, such as a camera, microphone, accelerometer, and the like. Any of the data mentioned herein can be output from one component to another component and can be output to the user.

A computer system can include a plurality of the same components or subsystems, e.g., connected together by external interface 1181, by an internal interface, or via removable storage devices that can be connected and removed from one component to another component. In some embodiments, computer systems, subsystem, or apparatuses communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an APSIC or FPGA) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application can be implemented as software code to be executed by a processor using any suitable computer language such as, for example, Java, C, C++, C #, Objective-C, Swift, or scripting language such as Perl or Python using, for example, conventional or object-oriented techniques. The software code can be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium can be any combination of such storage or transmission devices.

Such programs can also be encoded and transmitted using carrier signals adapted for transmission via wired, optical, and/or wireless networks conforming to a variety of protocols, including the Internet. As such, a computer readable medium can be created using a data signal encoded with such programs. Computer readable media encoded with the program code can be packaged with a compatible device or provided separately from other devices (e.g., via Internet download). Any such computer readable medium can reside on or within a single computer product (e.g. a hard drive, a CD, or an entire computer system), and can be present on or within different computer products within a system or network. A computer system can include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps can be used with portions of other steps from other methods. Also, all or portions of a step can be optional. Additionally, any of the steps of any of the methods can be performed with modules, units, circuits, or other means of a system for performing these steps.

The specific details of particular embodiments can be combined in any suitable manner without departing from the spirit and scope of embodiments of the invention. However, other embodiments of the invention can be directed to specific embodiments relating to each individual aspect, or specific combinations of these individual aspects.

Although the foregoing embodiments have been described in some detail for purposes of clarity of understanding, the invention is not limited to the details provided. There are many alternative ways of implementing the invention. The disclosed embodiments are illustrative and not restrictive. The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component is merely to distinguish between components and does not limit the referenced components to a particular location or order unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A system for updating a sequencing cell, the system comprising:
a fluid chamber comprising a first electrolyte reservoir of the sequencing cell, a second electrolyte reservoir of the sequencing cell, and a membrane that divides the first electrolyte reservoir from the second electrolyte reservoir, wherein the membrane comprises an initial nanopore, and wherein the first electrolyte reservoir has a first initial osmolarity and the second electrolyte reservoir has a second initial osmolarity;
a flow subsystem that controls a flow of a solution to the first electrolyte reservoir;
a plurality of replacement nanopores;
a voltage source configured to apply a voltage across the membrane; and
a processor communicably coupled with the voltage source and the flow subsystem and configured to perform operations comprising:
flowing a first electrolyte solution to the first electrolyte reservoir, wherein the first electrolyte solution has a first electrolyte solution osmolarity that is different than the first initial reservoir osmolarity, thereby causing the first electrolyte reservoir to have a new osmolarity that is different than the first initial osmolarity, so as to eject the initial nanopore from the membrane;
adding a second electrolyte solution to the first electrolyte reservoir, wherein the second electrolyte solution comprises the plurality of replacement nanopores, and wherein the second electrolyte solution has a second electrolyte solution osmolarity that is closer to the second initial osmolarity than the first electrolyte solution osmolarity; and
applying a voltage across the membrane so as to insert one of the plurality of replacement nanopores into the membrane.

2. The system of claim 1, further comprising:
a detector configured to record a measurement of an osmolarity, wherein the processor is communicably connected to a detector.

3. The system of claim 2, wherein the detector is configured to record the measurement of the osmolarity of an effluent exiting the first electrolyte reservoir.

4. The system of claim 3, wherein the operations further comprise:
comparing the measurement to a preselected osmolarity for controlling a flow into the first electrolyte reservoir.

5. The system of claim 4, wherein the operations further comprise:
generating a signal if the measurement exceeds or equals the preselected osmolarity; and
stopping the flowing of the first electrolyte solution in response to the signal.

6. The system of claim 4, wherein the operations further comprise:
generating a signal if the preselected osmolarity exceeds or equals the measurement; and
stopping the flowing of the second electrolyte solution in response to the signal.

7. The system of claim 1, further comprising:
one or more valves or pumps configured to adjust the flowing of the first electrolyte solution and the adding of the second electrolyte solution, wherein the processor is communicably connected to each of the one or more valves or pumps.

8. The system of claim 1, wherein an initial nanopore complex comprises the initial nanopore, an initial template, and an initial polymerase; and wherein each of a plurality of replacement nanopore complexes comprises one of the plurality of replacement nanopores, a replacement template, and a replacement polymerase.

9. The system of claim 1, wherein the voltage source is an alternating current voltage source.

* * * * *